US007943795B2

(12) United States Patent
Gossett et al.

(10) Patent No.: US 7,943,795 B2
(45) Date of Patent: May 17, 2011

(54) VITAMIN D RECEPTOR MODULATORS

(75) Inventors: Lynn Stacy Gossett, Indianapolis, IN (US); Jose Eduardo Lopez, Fishers, IN (US); Alan M. Warshawsky, Carmel, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 997 days.

(21) Appl. No.: 11/721,109

(22) PCT Filed: Dec. 19, 2005

(86) PCT No.: PCT/US2005/046360

§ 371 (c)(1),
(2), (4) Date: Jun. 7, 2007

(87) PCT Pub. No.: WO2006/069153

PCT Pub. Date: Jun. 29, 2006

(65) Prior Publication Data

US 2009/0234001 A1 Sep. 17, 2009

Related U.S. Application Data

(60) Provisional application No. 60/637,930, filed on Dec. 21, 2004.

(51) Int. Cl.
*C07C 63/00* (2006.01)

(52) U.S. Cl. ........ 562/405; 514/475; 514/741; 560/100; 568/715; 568/722

(58) Field of Classification Search ........................ None
See application file for complete search history.

(56) References Cited

U.S. PATENT DOCUMENTS

| | | | | |
|---|---|---|---|---|
| 6,218,430 | B1 * | 4/2001 | Allegretto et al. | 514/475 |
| 6,706,725 | B1 | 3/2004 | Bernardon | |
| 2006/0094778 | A1 | 5/2006 | Nagpal et al. | |
| 2006/0135484 | A1 | 6/2006 | Nagpal et al. | |
| 2006/0287536 | A1 | 12/2006 | Dahnke et al. | |
| 2006/0293385 | A1 | 12/2006 | Gajewski et al. | |
| 2007/0105951 | A1 | 5/2007 | Gajewski et al. | |
| 2007/0106095 | A1 | 5/2007 | Lu et al. | |
| 2007/0149810 | A1 | 6/2007 | Lu et al. | |

FOREIGN PATENT DOCUMENTS

| | | |
|---|---|---|
| WO | WO 2004/048309 | 6/2004 |
| WO | WO 2005/051893 | 6/2005 |
| WO | WO 2006/069154 | 6/2006 |

OTHER PUBLICATIONS

Boehm, M.F. et al, "Novel nonsecosteroidal vitamin D mimics exert VDR-modulating activities with less calcium mobilization than 1,25-dihydroxyvitamin D3", Chemistry and biology, Current Biology, London, GB, vol. 6, No. 5, May 1999, pp. 265-275, XP004881420, ISSN: 1074-5521.

Nagpal, S. et al. "Vitamin D Analogs: Mechanism of Action of Therapeutic Applications", *Curr. Med. Chem.* 2001, 1661-1679, vol. 8.

Bouillon R., et al. Structure-Function Relationships in the Vitamin D Endocrine System, Endocrine Rev. 1995, 200-257, vol. 16.

Swann et al. "Rational Design of Vitamin D3 Analogues Which Selectively Restore Activity to a Vitamin D Receptor Mutant Associated with Rickets" *Org. Lett.* 2002, p. 1863- 3866 vol. 4.

Swann et al. "Structure-Based Design of Selective Agonists for a Rickets-Associated Mutant of the Vitamin D Receptor" *J. Am. Chem. Soc.* 2002 13795-13805, vol. 124.

Basak, et al., "Comparative effects of calcipotriol and betamethasone 17-valerate solution in the treatment of seborrhoeic dermatitis of the scalp," *European Academy of Dermatology and Venereology JEADV*, vol. 15, pp. 77-92 (2001).

Böhm, et al., "Disseminated superficial actinic porokeratosis: Treatment with topical tacalcitol," *Journal of the American Academy of Dermatology*, vol. 40, pp. 479-480.

Cunningham, et al., "Topical calcipotriene for morphea/linear Scleroderma," *Journal of the American Academy of Dermatology*, vol. 39, pp. 211-215 (1998).

Harrison, "Disseminated superficial actinic porokeratosis responding to calcipotriol," *Clinical Exp. Dermatol.*, vol. 19, No. 1, p. 95 (1994).

Lin, et al., "The pleiotropic actions of vitamin D," *BioEssays*, vol. 26, pp. 21-28 (2003).

Lu, et al., "Transcriptional Profiling of Keratinocytes Reveals a Vitamin D-Regulated Epidermal Differentiation Network," *The Journal of Investigative Dermatology* vol. 124, pp. 778-785 (2005).

Nakayama, et al., "Four cases of sebopsoriasis or seborrheic dermatitis of the face and scalp successfully treated with 1a-24(R)-dihydroxycholecalciferol (tacalcitol) cream," *European Journal of Dermatology* vol. 10, No. 7, pp. 528-532, (2000).

Sapadin, et al., "Treatment of Scleroderma," *Arch Dermatology*, vol. 138, pp. 99-105 (2002).

Sato, et al., "Epidermal Growth Factor and 1α, 25-Dihydroxyvitamin $D_3$ Suppress Kipogenesis in Hamster Sebaceous Gland Cells In Vitro," *The Society of Investigative Dermatology*vol. 117, pp. 965-970 (2001).

Yee, et al., "Vitamin D Receptor Modulators for Inflammation and Cancer," *Mini-Reviews in Medicinal Chemistry*, vol. 5, No. 8, pp. 761-778 (2005).

Zasloff, "Sunlight, Vitamin D, and the Innate Defenses of the Human Skin," *The Society for Investigative Dermatology*, vol. 125, pp. xi125, pp. xvi-xvii (2005).

Zinser, et al., "Vitamin $D_3$ receptor ablation sensitizes skin to chemically induced tumorigenesis," *Carcinogenesis*, vol. 23, No. 12, pp. 2103-2109 (2002).

Hayashi, N. et al., "Comedolytic effect of topically applied active vitamin D3 analogue on pseudocomedones in the rhino mouse." British Journal of Dermatology, 2006, 155, pp. 895-901.

* cited by examiner

*Primary Examiner* — Sudhakar Katakam
(74) *Attorney, Agent, or Firm* — James B. Myers

(57) ABSTRACT

The present invention relates to novel, non-secosteroidal, phenyl-naphthalene compounds of Formula (I): wherein R, R1, RP, $Z_P$, $L_{P1}$, $L_{P2}$ $L_{NP}$, $RP_3$, RN, and $Z_{NP}$ are defined herein, their preparation, pharmaceutical compositions, and methods of use.

(I)

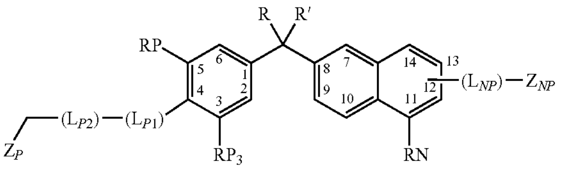

12 Claims, No Drawings

VITAMIN D RECEPTOR MODULATORS

REFERENCE TO RELATED APPLICATION

This application is submitted as a United States national phase entry, pursuant to 35 U.S.C. §371, of PCT/US2005/046360, filed on 19 Dec. 2005, which claims the benefit of U. S. provisional patent application Ser. No. 60/637,930, filed 21 Dec. 2004, each of which is incorporated by reference herein.

BACKGROUND OF THE INVENTION

Vitamin D Receptor (VDR) is a ligand dependent transcription factor that belongs to the superfamily of nuclear hormone receptors. The VDR protein is 427 amino acids, with a molecular weight of ~50 kDa. The VDR ligand, 1α,25-dihydroxyvitamin D3 (the hormonally active form of Vitamin D) has its action mediated by its interaction with the nuclear receptor known as Vitamin D receptor ("VDR"). The VDR ligand, 1α,25-dihydroxyvitamin D3 (1α,$25(OH)_2D_3$) acts upon a wide variety of tissues and cells both related to and unrelated to calcium and phosphate homeostasis.

The activity of 1α,25-dihydroxyvitamin D3 in various systems suggests wide clinical applications. However, use of conventional VDR ligands is hampered by their associated toxicity, namely hypercalcemia (elevated serum calcium). Currently, 1α,$25(OH)_2D_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of 1α,$25(OH)_2D_3$) show increased separation of binding affinity on VDR from hypercalcemic activity.

Chemical modifications of 1α,$25(OH)_2D_3$ have yielded analogs with attenuated calcium mobilization effects (R. Bouillon et. al., *Endocrine Rev.* 1995, 16, 200-257). One such analog, Dovonex® pharmaceutical agent (product of Bristol-Meyers Squibb Co.), is currently used in Europe and the United States as a topical treatment for mild to moderate psoriasis (K. Kragballe et. al., *Br. J. Dermatol.* 1988, 119, 223-230).

Other Vitamin $D_3$ mimics have been described in the publication, *Vitamin D Analogs: Mechanism of Action of Therapeutic Applications*, by Nagpal, S.; Lu, J.; Boehm, M. F., *Curr. Med. Chem.* 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Another major disorder that could benefit from VDR mediated biological activity is psoriasis. Psoriasis is one of the most common dermatologic diseases and is a chronic inflammatory skin condition characterized by erythematosus, sharply demarcated papules and rounded plaques, covered by silvery micaceous scale.

Synthetic VDR ligands with reduced calcemic potential have been synthesized. For example, a class of bis-phenyl compounds stated to mimic 1α,25-dihydroxyvitamin $D_3$ is described in U.S. Pat. No. 6,218,430 and the article; "Novel nonsecosteroidal vitamin D mimics exert VDR-modulating activities with less calcium mobilization than 1α,25-Dihydroxyvitamin $D_3$" by Marcus F. Boehm, et. al., *Chemistry & Biology* 1999, Vol 6, No. 5, pgs. 265-275.

Synthetic VDR ligands having an aryl-thiophene nucleus are described in U.S. provisional patent application Ser. No. 60/384,151, filed 29 May 2002 (WO 03/101,978), and synthetic VDR ligands having phenyl-benzoxazole nucleus are described in U.S. provisional patent application Ser. No. 60/638,029 filed 21 Dec. 2004.

There remains a need for improved treatments using alternative or improved pharmaceutical agents that mimic 1α,25-dihydroxyvitamin $D_3$ to stimulate bone formation, restore bone quality, and treat other diseases without the attendant disadvantage of hypercalcemia.

SUMMARY OF THE INVENTION

Novel compounds having a phenyl-naphthalene nucleus of Formula "(PN)" have been found effective as Vitamin D Receptor modulators (VDRM):

(PN)

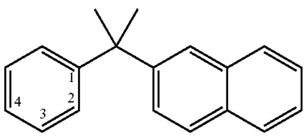

Compounds of the invention with VDR modulating activities are represented by Formula I (I)

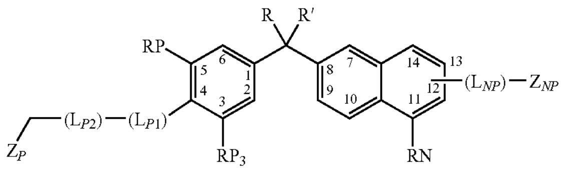

wherein the variables R, R', RP, $RP_3$, $L_{P1}$, $L_{P2}$, $Z_P$, RN, $L_{NP}$, and $Z_{NP}$ are as hereinafter defined.

In another aspect, the present invention is directed towards pharmaceutical compositions containing pharmaceutically effective amounts of compounds of Formula I or a pharmaceutically acceptable salt or a prodrug thereof, either singly or in combination, together with pharmaceutically acceptable carriers and/or auxiliary agents.

Another aspect of the invention is a pharmaceutical formulation for treatment or prevention of osteoporosis containing pharmaceutically effective amounts of the vitamin D receptor modulator compound of Formula I alone or together with pharmaceutically effective amounts of co-agents conventionally used for the treatment of osteoporosis.

Another aspect of the invention is a pharmaceutical formulation for treatment or prevention of psoriasis containing pharmaceutically effective amounts of the vitamin D receptor modulator compound of Formula I alone or together with pharmaceutically effective amounts of co-agents conventionally used for the treatment of psoriasis.

Another aspect of the invention is a pharmaceutical formulation for treatment or prevention of prostate cancer containing pharmaceutically effective amounts of the vitamin D receptor modulator compound of Formula I alone or together with pharmaceutically effective amounts of co-agents conventionally used for the treatment of prostate cancer.

Another aspect of the invention is to use the compounds of Formula I to treat disease states responsive to Vitamin D receptor ligands.

Another aspect of the invention is the prevention and treatment of acne, actinic keratosis, alopecia, Alzheimer's disease, autoimmune induced diabetes, benign prostatic hyperplasia, bladder cancer, bone fracture healing, breast cancer, Crohn's disease, prostate cancer, colon cancer, Type I diabetes, host-graft rejection, hypercalcemia, Type II diabetes, leukemia, multiple sclerosis, insufficient sebum secretion, osteomalacia, osteoporosis, insufficient dermal firmness, insufficient dermal hydration, myelodysplastic syndrome, psoriatic arthritis, psoriasis, renal osteodystrophy, rheumatoid arthritis, scleroderma, seborrheic dermatitis, skin cancer, systemic lupus erythematosis, skin cell damage from mustard vesicants, ulcerative colitis, and wrinkles, by administering to a mammal in need thereof a pharmaceutically effective amount of a compound of Formula I.

DETAILED DESCRIPTION OF THE INVENTION

Definitions:

The term, "abscess" refers to adverse complications often associated with surgery, trauma, or diseases that predispose the host to abscess formation from encapsulated bacteria lymphocytes, macrophages, and etc.

The term, "adhesion" refers to the adverse and abnormal union of surfaces normally separate by the formation of new fibrous tissue resulting from an inflammatory process.

The term, "compound of the invention" refers to a compound represented by Formula I or as set out as products of the Examples or synthesis schemes described herein.

The term, "Active Ingredient" means a compound of the invention.

The term, "mustard" is inclusive of both sulfur mustards and nitrogen mustards, either alone or in any combination. Exemplary of such compounds are the vesicants; bis(2-chloroethyl)sulfide (Chemical Agent Symbol HD), $Cl(CH_2)_2S(CH_2)_2Cl$ 1,2-bis(2-chloroethylthio)ethane (Chemical Agent Symbol Q), $Cl(CH_2)_2S(CH_2)_2S(CH_2)_2Cl$; bis(2-chloroethylthioethyl)ether, $Cl(CH_2)_2S(CH_2)O(CH_2)_2S(CH_2)_2Cl$ (Chemical Agent Symbol T); tris(2-chloroethyl)amine (Chemical Agent Symbol HN3) $N(CH_2CH_2Cl)_3$; N-methyl-2,2'-dichlorodiethylamine (Chemical Agent Symbol NH2); and 2,2'-dichlorotriethylamine, $CH_3CH_2N(CH_2CH_2Cl)_2$ (Chemical Agent Symbol NH1).

The term heteroaryl as used herein refers to the heteroaryls illustrated below:

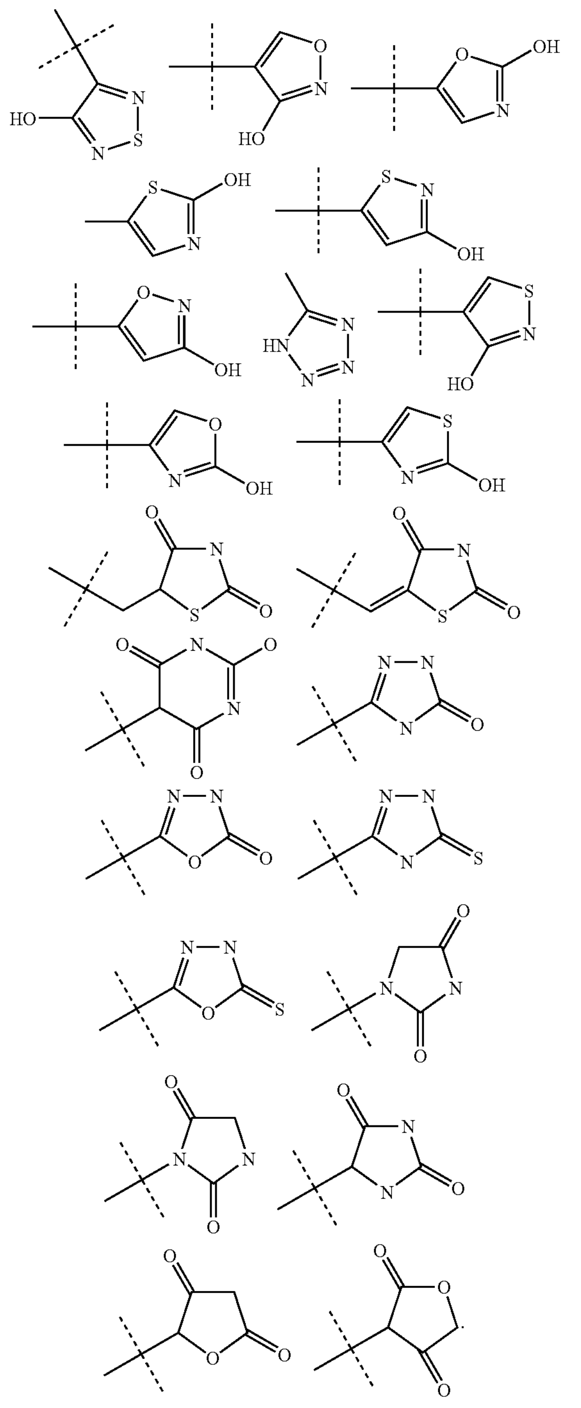

where the dotted line crossing a solid line symbol represents a bond of attachment between the atom of the radical and the rest of the molecule.

The term, "(Acidic Group)" means an organic group that acts as a proton donor capable of hydrogen bonding. Illustrative of an (Acidic Group) is a group selected from the following: carboxylic acid, acylsulfonamide, tetrazolyl, substituted heteroaryls with acidic hydrogens, i.e., hydroxyl groups.

The term, "mammal" includes humans.

The terms "halo" and halogen refer to fluorine, chlorine, bromine, and iodine. Preferred halogens for the present invention include fluorine.

Unless specified herein, chemical terms are used in their customary usage as understood by one skilled in the art.

The term, "$C_{1-3}$ alkyl" refers to an alkyl group selected from methyl, ethyl, n-propyl, and isopropyl. The abbreviations, "Me" means methyl; "Et" means ethyl; "iPr" or "i-Pr" means 1-methylethyl; and "tBu" or "t-Bu" means 1,1-dimethylethyl.

The term, "branched $C_3$-$C_5$ alkyl" is an alkyl group selected from 1-methylethyl; 1-methylpropyl; 2-methylpropyl; 1,1-dimethylethyl; 1,1-dimethylpropyl; 1,2-dimethylpropyl; or 2,2-dimethylpropyl. Preferred branched $C_3$-$C_5$ alkyl groups are 2-methylpropyl and 1,1-dimethylethyl, with the 1,1-dimethylethyl group being most preferred.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. It will be understood that alkenyl groups can include one or more double bonds. Further, the alkenyl groups can include positional isomers about the double bonds i.e. trans (Z) or cis (E) isomers. Suitable alkenyl groups have from 2 to about 20 carbon atoms. It also will be understood by those skilled in the art that compounds of the present invention can exist in two or more tautomeric forms. All such tautomeric forms are contemplated to be included within the scope of the present invention.

The term "$C_1$-$C_5$ alkyl" refers to saturated aliphatic groups including straight-chain, branched-chain, and cyclic groups and any combinations thereof. Examples of $C_1$-$C_5$ alkyl groups are methyl, ethyl, n-propyl, from 1-methylethyl; n-butyl, 1-methylpropyl; 2-methylpropyl; 1,1-dimethylethyl; n-amyl, 1,1-dimethylpropyl; 1,2-dimethylpropyl; and 2,2-dimethylpropyl.

The term "cycloalkyl" includes organic radicals having 3 to 8 carbon atoms as ring members. Examples include: cyclopropyl, cyclobutyl, cyclopentyl and cyclohexyl. When substituted, the substituents can be selected from halo, hydroxyl, —CN, $C_1$-$C_3$ alkyl, —SH, —O$C_1$-$C_3$ alkyl, and —S$C_1$-$C_3$ alkyl.

The term, "cycloalkenyl" includes organic radicals having 3 to 8 carbon atoms as ring members; non-limiting examples include: cyclopropenyl, cyclobutenyl, cyclopentenyl and cyclohexenyl.

The term, "$C_1$-$C_5$ haloalkyl" is an alkyl group containing one or more halogen atoms. The term, "$C_1$-$C_5$ fluoroalkyl" is an alkyl group containing fluorine and includes organic radicals such as —$CF_3$, —$CHF_2$, —$CH_2F$, —$CF_2CF_3$, —$CHFCF_3$, —$CH_2CF_3$, —$CH_2CHF_2$, and —$CH_2CH_2F$, with —$CF_3$ being preferred.

The term, "hydroxyalkyl" means an alkyl group having at least one hydroxyl group. Non-limiting examples include: 3-methyl-3-hydroxypentyl, 3-methyl-3-hydroxypentenyl, 3-methyl-3-hydroxypentynyl, 3-ethyl-3-hydroxypentyl, 3-ethyl-3-hydroxypentenyl, 3-ethyl-3-hydroxypentynyl, 3-ethyl-3-hydroxy-4-methylpentyl, 3-ethyl-3-hydroxy-4-methylpentenyl, 3-ethyl-3-hydroxy-4-methylpentynyl, 3-propyl-3-hydroxypentyl, 3-propyl-3-hydroxypentenyl, 3-propyl-3-hydroxypentynyl, 1-hydroxy-2-methyl-1-(methylethyl)propyl, 2-methyl-3-hydroxy-4,4-dimethylpentyl, 2-methyl-3-hydroxy-3-ethylpentyl, 2-ethyl-3-hydroxy-3-ethylpentyl, 2-ethyl-3-hydroxy-4,4-dimethylpentyl, 1-hydroxycycloalkenyl; and 1-hydroxycycloalkyl.

The term "hydroxycycloalkyl" refers to a radical having the general structural formula:

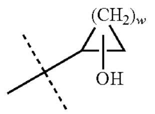

where w is an integer from 1 to 6 and the hydroxyl radical is substituted on any ring carbon atom. Examples include: 2-hydroxycyclohexylmethyl, 3-methyl-2-hydroxycyclohexyloxy, 3-methyl-2-hydroxycyclohexylmethyl, and 3,3-dimethyl-2-hydroxycyclohexyloxy.

The term "1-hydroxycycloalkyl" refers to a radical having the general structural formula:

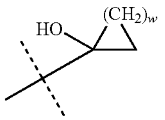

where w is defined as above. Examples of 1-hydroxycycloalkyl radicals include: 1-hydroxycyclopropyl, 1-hydroxycyclobutyl, 1-hydroxycyclopentyl, 1-hydroxycyclohexyl, 1-hydroxycycloheptyl, and 1-hydroxycyclooctyl.

The term oxocycloalkyl refers to a radical having the general structural formula:

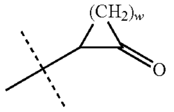

where w is defined as above. The bond of attachment of the oxocycloalkyl to the referenced molecule need not be restricted to the carbon adjacent to the carbonyl carbon, but can be attached via any of the carbon atoms making up the rings. Non-limiting examples of oxocycloalkyl radicals include: 2-oxocyclohexyloxy, 2-oxocyclohexylmethyl, 3-methyl-2-oxocyclohexyloxy, 3-methyl-2-oxocyclohexylmethyl, 3,3-dimethyl-2-oxocyclohexyloxy, 3,3-dimethyl-2-oxocyclohexylmethyl, and 2-hydroxycyclohexyloxy.

Certain compounds of the invention exist in isomeric configurations with chiral centers, i.e., diastereomers and enantiomers. Each of the isomeric forms of the compounds is contemplated to be within the scope of the present invention. Each of the various isomers can be prepared as single isomers and/or separated into single isomers by techniques known to those skilled in the art. Therefore, the compounds of the present invention can be used either as single isomer or isomeric form or alternatively the compounds of the present invention can be used as a combination of isomers. The "jagged" bond illustrated below is used to represent that carbon to which it is attached can exist as either configuration, i.e., R or S.

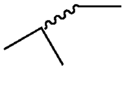

It also will be understood by those skilled in the art that compounds of the present invention can exist in two or more tautomeric forms. All such tautomeric forms are contemplated to be included within the scope of the present invention.

Compounds of the Invention:

The compounds of the invention with vitamin receptor modulating (VDRM) activity are represented by Formula (I) or a pharmaceutically acceptable salt or a prodrug derivative thereof:

(I)

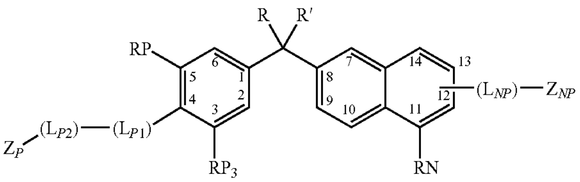

wherein

R and R' are independently $C_1$-$C_5$ alkyl, $C_1$-$C_5$ haloalkyl, or together R and R' form a substituted or unsubstituted, saturated or unsaturated cycloalkyl ring having from 3 to 8 carbon atoms;

$RP_3$ and RN are independently selected from the group consisting of hydrogen, halo, $C_1$-$C_5$ alkyl, $C_1$-$C_5$ haloalkyl, —O—$C_1$-$C_5$ alkyl, —S—$C_1$-$C_5$ alkyl, —O—$C_1$-$C_5$ haloalkyl, —CN, —$NO_2$, acetyl, —S—$C_1$-$C_5$ haloalkyl, $C_2$-$C_5$ alkenyl, $C_3$-$C_5$ cycloalkyl, and $C_3$-$C_5$ cycloalkenyl;

RP is selected from: hydrogen, halo, $C_1$-$C_5$ alkyl, $C_1$-$C_5$ haloalkyl, —O—$C_1$-$C_5$ alkyl, —S—$C_1$-$C_5$ alkyl, —O—$C_1$-$C_5$ haloalkyl, —CN, —$NO_2$, acetyl, —S—$C_1$-$C_5$ haloalkyl, $C_2$-$C_5$ alkenyl, $C_3$-$C_5$ cycloalkyl, and $C_3$-$C_5$ cycloalkenyl;

$(L_{P1})$, $(L_{P2})$, and $(L_{NP})$ are divalent linking groups independently selected from the group consisting of: a bond, —$(CH_2)_m$—C(OH)—, —$(CH_2)_m$—O—, —$(CH_2)_m$—S—, —$(CH_2)_m$—S(O)—, —$(CH_2)_m$—$S(O)_2$—, —$(CH_2)_m$—N(R40)-, —$(CH_2)_m$—C(R40)(R41)-, —$(CH_2)_m$—C(O)—, —N(R40)-C(O)—, —$(CH_2)_m$—CH═CH—, and —$(CH_2)_m$—C≡C—;

where m is 0-5;

R40 and R41 each is independently selected from: hydrogen, $C_1$-$C_5$ alkyl, $C_1$-$C_5$ hydroxyalkyl, $C_1$-$C_5$ haloalkyl, $C_2$-$C_5$ alkenyl, $C_3$-$C_5$ cycloalkyl, $C_3$-$C_5$ cycloalkenyl;

$Z_P$ is selected from: branched $C_3$-$C_5$ alkyl, $C_3$-$C_{10}$ hydroxyalkyl, $C_3$-$C_{10}$ hydroxyalkenyl, $C_3$-$C_{10}$ hydroxyalkynyl, $C_3$-$C_{10}$ hydroxycycloalkyl, $C_4$-$C_{10}$ hydroxy cycloalkenyl, and oxocycloalkyl;

$Z_{NP}$ is selected from: $C_1$-$C_5$ alkyl, $C_2$-$C_5$ alkenyl, $C_3$-$C_5$ cycloalkyl, $C_3$-$C_5$ cycloalkenyl, $C_1$-$C_5$ hydroxyalkyl, $C_1$-$C_5$ haloalkyl, $C_1$-$C_5$ alkylaryl, $C_1$-$C_5$ hydroxyalkylaryl, $C_0$-$C_5$ alkyl-$CO_2H$, $C_0$-$C_3$ alkyl-cycloalkyl-$CO_2H$, $C_0$-$C_5$ alkyl-N(R40)(R41), —X—($C_1$-$C_5$ alkyl), —X—($C_1$-$C_5$ alkenyl), —X—($C_3$-$C_5$ cycloalkyl), —X—($C_3$-$C_5$ cycloalkenyl), —X—($C_1$-$C_5$ haloalkyl), —X—($C_1$-$C_5$ hydroxyalkyl), —X—($C_1$-$C_5$ alkylaryl), —X($OC_1$-$C_5$ alkyl), —XN(R40)(R41), —XN(R40)aryl, —N($CH_3$)($OCH_3$), —N(OH)($CH_3$), —N(R42)-($C_1$-$C_5$ alkyl)$CO_2H$, —N(R42)-($C_1$-$C_5$ alkyl)C(O)($C_1$-$C_5$ alkyl), —N(R42)-($C_1$-$C_5$ alkyl)C(O)($OC_1$-$C_5$ alkyl), —N(R42)-$SO_2$—($C_1$-$C_5$ alkyl), —N(R42)-S(O)—($C_1$-$C_5$ alkyl), —P(O)—($OC_1$-$C_5$ alkyl)$_2$, heteroaryl, and —N═C(R40)N(R40)(R41);

R42 is selected from: H, $C_1$-$C_3$ alkyl, and $C_1$-$C_3$ haloalkyl; and

X is selected from: O, C(O), C(S), S(O), and $SO_2$;

provided that -$(L_{NP})$-$Z_{NP}$ is substituted at either the 12 or 13 position of the naphthalene ring; or a pharmaceutically acceptable salt, solvate, prodrug, enantiomer, racemate, diastereomer or mixture of diastereomers thereof.

It will be understood by those skilled in the art that the individual groups listed herein for the divalent linkers, $(L_{P1})$, $(L_{P2})$, and $(L_{NP})$, can be attached at either end to the benzoxazole nucleus. For example, for the linker, —N(R40)-C(O)—, either the nitrogen can be attached to the naphthalene nucleus or alternatively the carbonyl carbon can be attached to the naphthalene nucleus.

In preferred embodiments, compounds of the invention include the compound of Formula I having as preferred substituents;

R and R' are independently methyl or ethyl;

RP is hydrogen or methyl;

$RP_3$ and RN are independently hydrogen, methyl, ethyl, —O-methyl, or cyclopropyl;

$(L_{P1})$ is a bond;

$(L_{P2})$ is a bond, —$CH_2$—, —CH(OH)—, or —C(Me)OH—;

$(L_{NP})$ is a bond, —C(O)—, —C(O)NH—, or —C(O)N(Me)—;

$Z_P$ is 1,1-dimethylethyl, 1-hydroxycyclopentyl, 1-hydroxycyclohexyl, 3-ethyl-3-hydroxypentyl, 3-ethyl-3-hydroxypentenyl, or 3-ethyl-3-hydroxypentynyl, $Z_{NP}$ is —$CO_2H$, —$CO_2$(R40), —N(R40)(R41), —NH—C(Me)(OH)—C(O)OH, —C(O)NMe-$CH_2$—C(O)OH, —C(O)NMe-$CH_2$—C(O)OMe, —C(O)NMe-$CH_2$—C(O)OEt, —C(O)NMe-$CH_2$—C(O)OiPr, —C(O)NMe-$CH_2$—C(O)tBu, -cyclopropyl-C(O)OH, -cyclobutyl-C(O)OH, —C(O)NMe-C$(Me)_2$-C(O)OH, —C(O)N(R40)S(O)(R42), —C(O)N(R40)$SO_2$R42, —C(O)—N(R40)-5-tetrazolyl, —C(O)N(R40)-($C_1$-$C_5$ alkyl)-S(O)R42, —C(O)N(R40)-($C_1$-$C_5$ alkyl)-$S(O)_2$R42, $C_0$-$C_3$ alkyl(cycloalkyl)C(O)NH$SO_2$Me, $C_0$-$C_3$ alkyl-(cycloalkyl)-C(O)OH, $C_0$-$C_3$ alkyl-(cycloalkyl)-C(O)NH-heteroaryl, $C_0$-$C_3$ alkyl-(cycloalkyl)-NH$SO_2$($C_1$-$C_5$ alkyl), and —$CH_2CO_2H$.

Preferred compounds of the invention and salts and prodrug derivatives are represented by formulae C1 to C8 as follows:

C1)

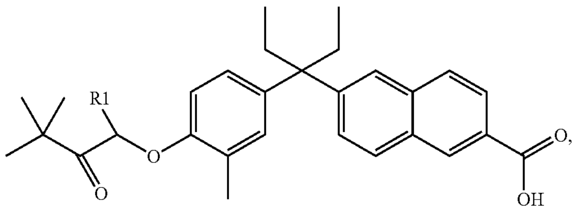

C2)

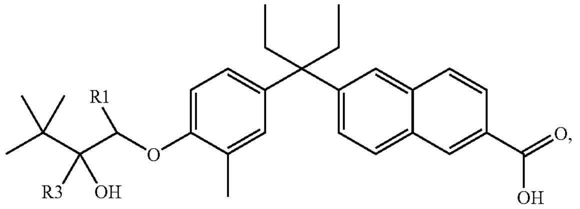

-continued

C3)

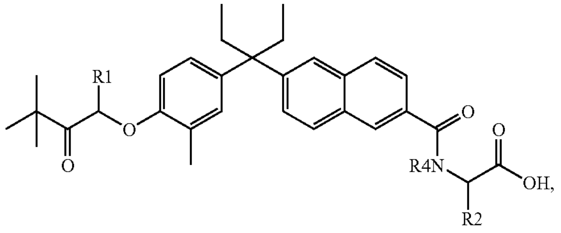

C4)

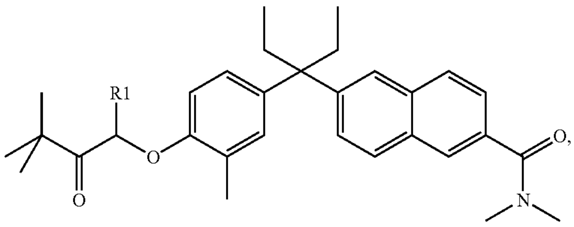

C5)

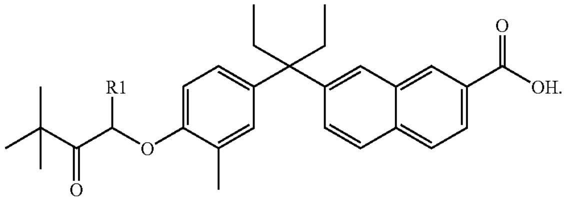

C6)

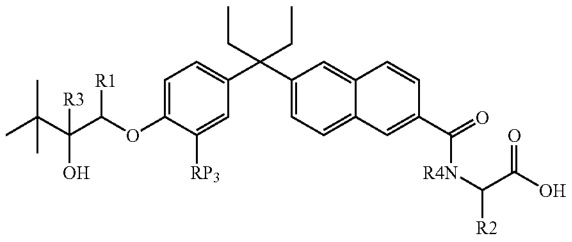

C7)

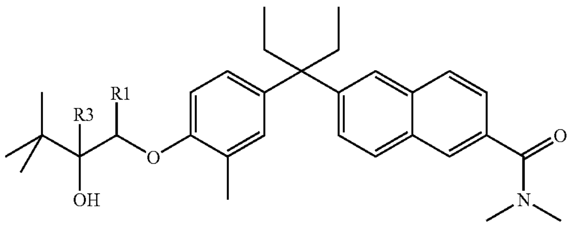

-continued

C8)

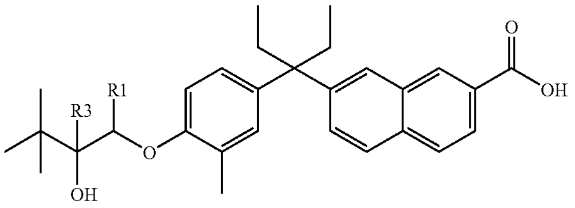

where R1 is H, Me, or Et; R2 is H or Me; R3 is H Me, or Et; and R4 is H or Me. Particularly preferred compounds include compounds represented by formulae C1-C8 where R1 is a Me or Et; and R2 and R3 individually are H or Me.

EXAMPLES

General Experimental Conditions:

The starting material/intermediate is the compound from the immediate preceding experimental unless otherwise indicated.

All reactions are performed under nitrogen/argon atmosphere, in a stirred reaction vessel, and at room temperature unless indicated otherwise.

Unless otherwise indicated, the notation that "organic layer is $MgSO_4/Na_2SO_4$ dried" "dryed over $MgSO_4/Na_2SO_4$" is defined as swirling or stirring the solution with a dessicant ($MgSO_4$ and/or $Na_2SO_4$) 5-15 m, then filtering off the dessicant to give an anhydrous filtrate.

For analogous multi-step reaction procedures, the yield is given either for the ultimate step or overall multi-steps as indicated.

Solutions are "concentrated" at a range of 25-75° C. with reduced pressure (0.05 to 1 mm).

Unless otherwise indicated, "the residue is chromatographed" is defined as silica gel chromatography of residue with moderate nitrogen pressure (flash chromatography) or a medium pressure chromatography systems using a silica gel to crude product ratio of ~10-100.

For HPLC, the conditions listed are for the analytical trace only. For Preparative HPLC, the eluent is similar to analytical HPLC eluent.

Thin layer chromatography is performed with silica gel plates with UV and/or appropriate staining solution.

NMR spectra are obtained with either 300 or 400 mHz spectrometer. NMR data is listed to denote spectrum is consistent with assigned structure. "NMR" notation without data denotes spectrum is consistent with assigned structure.

HRMS—high resolution mass spectrum

ES-MS—electrospray mass spectrum

Abbreviations:

Aq—aqueous d—day eq—equivalent h—hour m—minute satd—saturated disp—dispersion quant—quantitative rt for retention time (both small caps to minimize confusion with RT)

RT—room temperature

TABLE 1

| Chemical Terms | | | |
|---|---|---|---|
| Term | Definition | Term | Definition |
| BF3-OEt2 | boron trifluoride etherate | MeOH | methanol |
| BnBr | benzyl bromide | NMO | 4-methylmorpholine |
| CH2Cl2 | Dichloromethane | | N-oxide |
| DMAP | 4-(dimethylamino)pyridine | NMP | N-methylpyrrolidin- |
| DMF | N,N-dimethylformamide | | 2-one |
| DMSO | Dimethylsulfoxide | Na—S—R3 | sodium |
| DPPB | 1,4-bis(diphenylphosphino)butane | | alkylmercaptide |
| DPPF | dichloro[1,1'- | PBr3 | phosphorus |
| | bis(diphenylphosphino)ferrocene | | tribromide |
| EDCI | 3-Ethyl-1-[3-(dimethylamino)propyl]carbodiimide | Pd(DPPF) | palladium |
| | hydrochloride | | dichloro[1,1'- |
| EEDC | Diethyl cyanamide | | bis(diphenylphosphino)ferrocene |
| EtMgBr | ethyl magnesium bromide | Pd(OAc)2 | palladium (II) |
| EtOAc | ethyl acetate | | acetate |
| EtOH | Ethanol | Pd(TPP)4 | palladium |
| $H_2$ | hydrogen pressure | | tetrakistriphenylphosphine |
| H2NCH2CO2Me | methyl glycinate | Pd—C | palladium on carbon |
| Hept | Heptane | Pd—C/H2 | palladium on carbon |
| Hex | Hexanes | | with hydrogen |
| HN(OMe)Me | N-methyl-O-methyl | | pressure |
| | hydroxylamine | pTSA | para-toluenesulfonic |
| HNMe2 | dimethyl amine | | acid |
| HATU | O-(7-azabenzotriazol-1-yl)- | Pyr | pyridine |
| | N,N,N',N'-tetramethyl | Red-Al | sodium bis(2- |
| | uronium hexafluorophosphate | | methoxyethoxy)aluminum |
| HOAT | 7-aza-1-hydroxy benzotriazole | | hydride |
| HOBT | 1-hydroxybenzotriazole | R2MgBr | alkyl magnesium |
| K2CO3 | potassium carbonate | | bromide |
| LAH | Lithium aluminum hydride | R3MgBr | alkyl magnesium |
| LDA | Lithium diisopropyl amide | | bromide |
| LiHMDS | Lithium hexamethyl disilazide | R5MgBr | alkyl magnesium |
| Lindlar | Pd—$CaCO_3$—PbO | | bromide |
| catalyst | | R3S(O)2Cl | alkylsulfonyl |
| mCPBA | meta-chloroperbenzoic acid | | chloride |
| TPA | 12-O-tetradecanoyl 13-acetate | R2S(O)2NH2 | alkylsulfonamide |
| | (Sigma) | TBSCl | tert-butyldimethylsilyl |
| NaHMDS | Sodium hexamethyl disilazide | | chloride |
| NMM | N-methylmorpholine | tBuC(O)CH2Br— | 1-bromopinacolone |
| | | Tf2O | triflic anhydride |
| | | TFA | trifluoroacetic acid |
| | | THF | tetrahydrofuran |
| | | Ti(OiPr)4 | titanium |
| | | | tetraisopropoxide |
| | | TMS- | trimethylsilyl |
| | | acetylene | acetylene |
| | | TPAP | tetrapropylammonium |
| | | | perruthenate |
| | | BnHalide | benzylhalide |
| | | PHA | Phytohemagglutinin |
| | | | (Sigma) |

General Procedures

Scheme 1

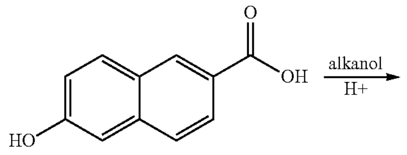

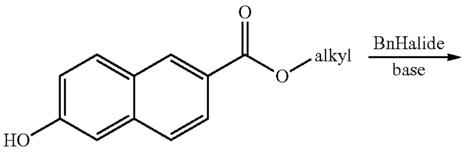

1.

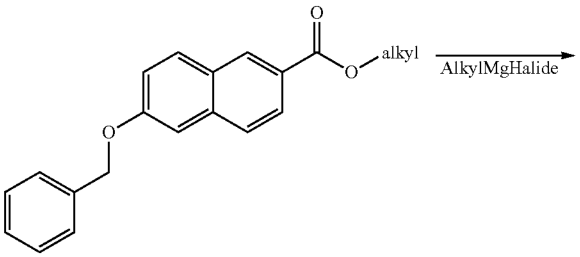

2.

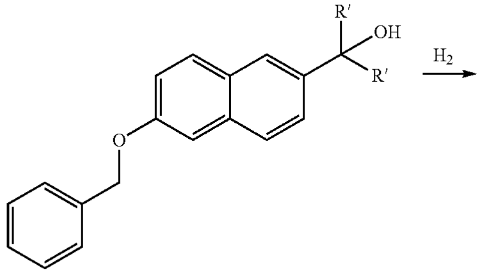

3.

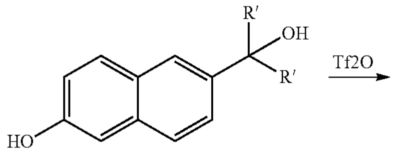

4.

-continued

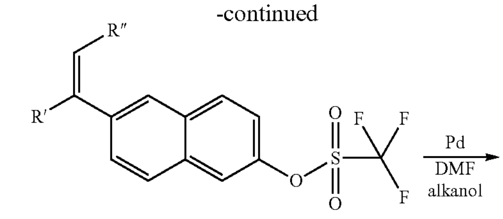

5.

Here, R″ means R′ minus a methylene group

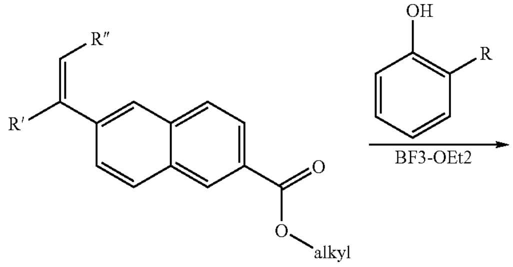

6.

Here, R″ means R′ minus a methylene group

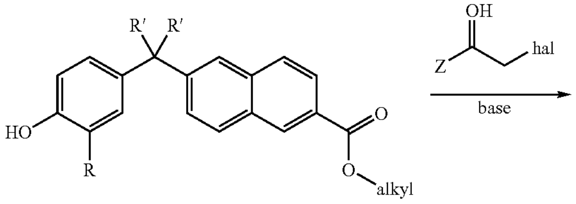

7.

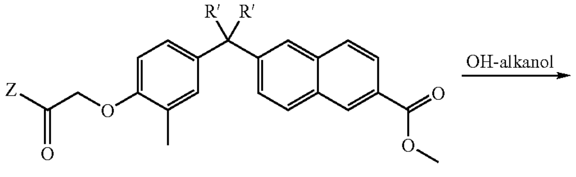

8.

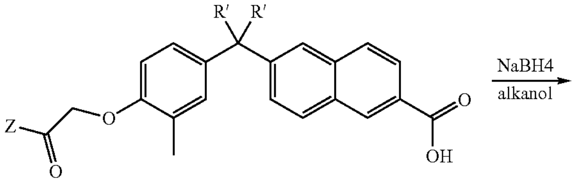

9.

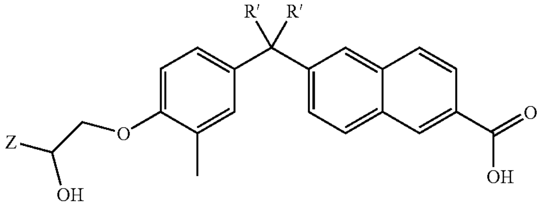

10.

6-Hydroxy-2-naphthoic acid is esterified in an alkanol with acid catalysis (HCl, sulfuric acid, or toluenesulfonic acid) from room temperature to the reflux temperature of the mixture to give the ester 1. Ester 1 is protected, e.g., with a benzylhalide and base to give the protected ester 2. Ester 2 is treated with excess alkyl Grignard reagent (2 to 5 equivalents) in diethylether or THF from 0° C. to room temperature to give the tert-carbinol 3. Carbinol 3 is hydrogenated with a catalyst, e.g., palladium on carbon to give the deprotected carbinol 4. Carbinol 4 is reacted with triflic anhydride to produce the triflate that dehydrates upon work up to the Z/E-olefin 5. Triflate 5 is reacted with carbon monoxide (1 to 100 psi) and a palladium catalyst (0.1 to 10%) in alkanol with DMF from room temperature to 150° C. for 8 to 48 h to give the ester 6. Ester 6 alkylates an ortho-substituted phenol in the presence of a Lewis acid, e.g., boron trifluoride etherate (0.01 to 5 equivalents) at room temperature to give the diarylmethane 7. A variety ortho-substituted phenols are commercially available or can be readily prepared by those skilled in the art. The free hydroxyl of the diarylmethane 7 is alkylated with an alpha-halo ketone (z-C(O)$CH_2$hal, where z is an alkyl group or a substituted alkyl group) to give keto ester 8. Keto ester 8 is saponified with lithium, sodium, or potassium hydroxide in alkanol from room temperature to the reflux temperature of the mixture to give the keto acid 9. Keto acid 9 is reduce to the carbinol 10. with lithium or sodium borohydride, or cyanoborohydride in alkanol at room temperature.

Scheme II.

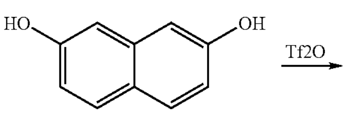

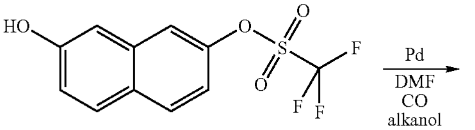

11.

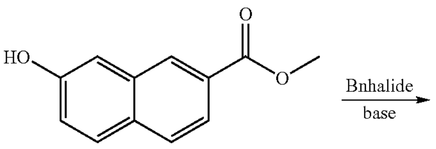

12.

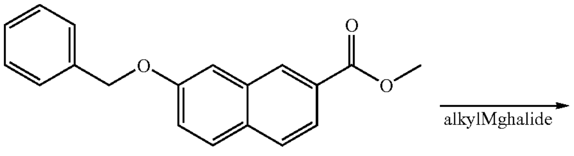

13.

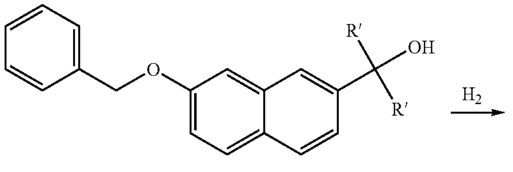

14.

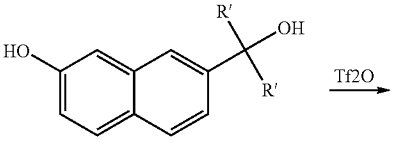

15.

-continued

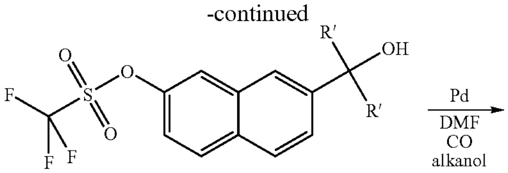

16.

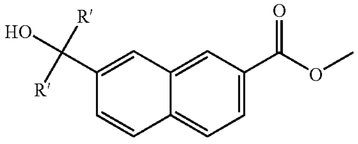

17.

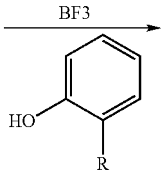

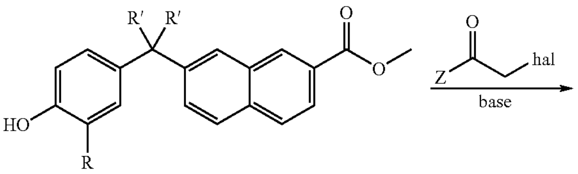

18.

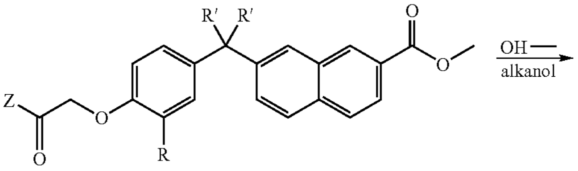

19.

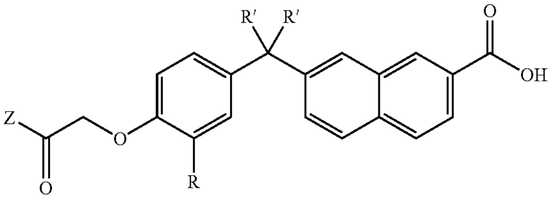

20.

Scheme II.

2,7-Dihydroxynaphthalene is reacted with triflic anhydride (0.9 to 1.3 equivalents) to produce the mono-triflate 11. Triflate 11 is reacted with carbon monoxide (1-100 psi) in DMF with alkanol and a palladium catalyst from room temperature to 150° C. and from 8 to 48 h to give the ester 12. The ester 12 is protected, e.g., with a benzylhalide and base to give the protected ester 13. Ester 13 is reacted with an excess of alkyl Grignard reagent (2-5 equivalents) to give the tert-carbinol 14. The protection group of 14 is removed, e.g., by hydrogenation in alkanol with a palladium catalyst to give the unprotected tert-carbinol 15. Carbinol 15 is converted to triflate 16. with triflic anhydride and base. Triflate 16 is converted to the ester 17 as above with carbon monoxide in DMF/alkanol and base in the presence of a palladium catalyst, e.g., palladium acetate and DPPB. Ester 17 alkylates an ortho-substituted phenol in the presence of a Lewis acid, e.g., boron trifluoride etherate (0.01 to 5 equivalents) at room temperature to give the diarylmethane 18. The free hydroxyl of the diarylmethane 18 is alkylated with an alpha-halo ketone(z-C(O)$CH_2$hal, where z is an alkyl group or a substituted alkyl group) to give keto ester 19. Keto ester 19 is saponified with lithium, sodium, or potassium hydroxide in alkanol from room temperature to the reflux temperature of the mixture to give the keto acid 20. Reduction of keto acid 20 to the carbinol is achieved as above with lithium or sodium borohydride or cyanoborohydride in alkanol at room temperature.

Each of the free acids produced in each of the above schemes (9, 10, and 20) are converted to esters and carboxamides using reactions well known to those skilled in the art.

Scheme III

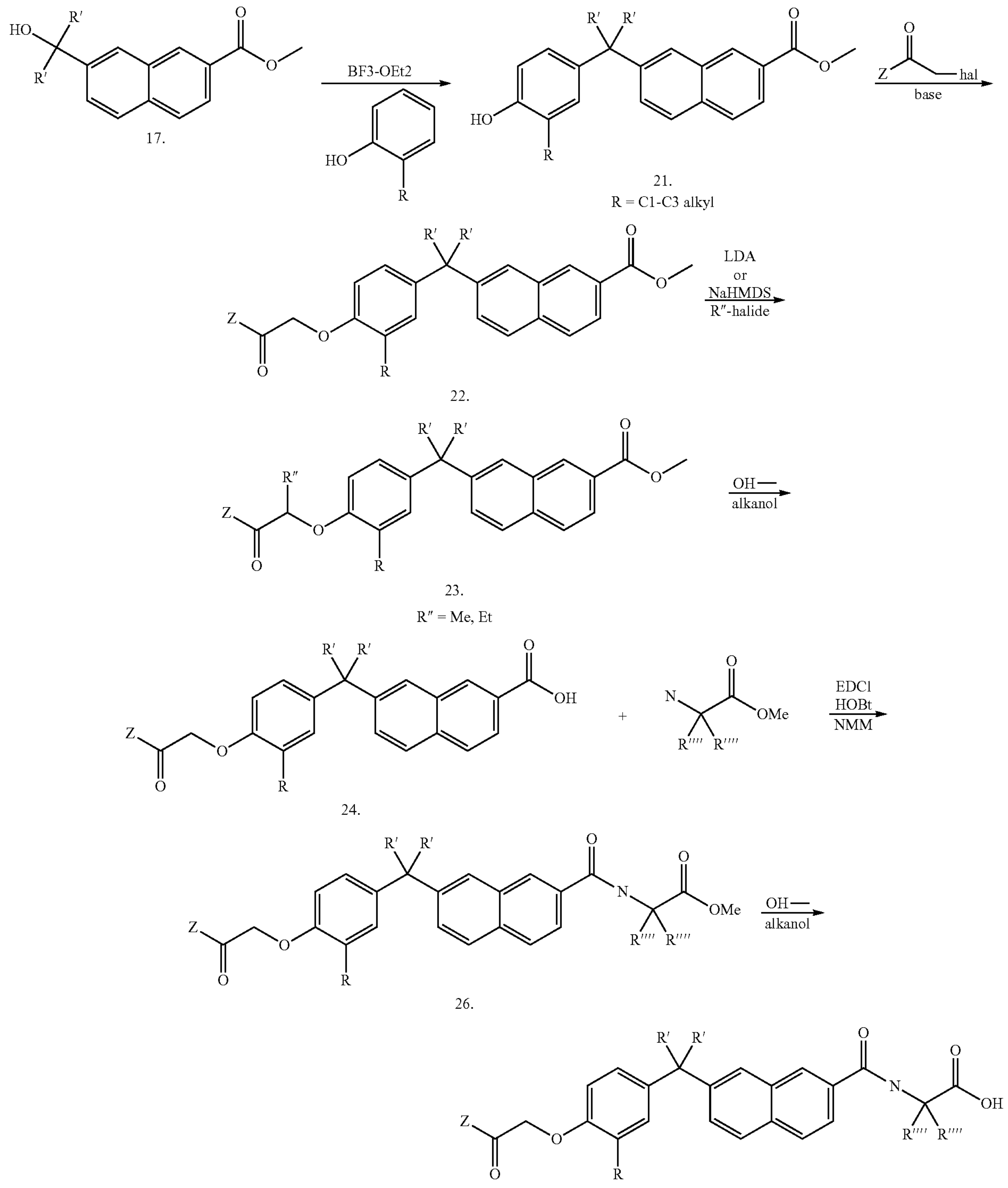

17.

21.

R = C1-C3 alkyl

22.

23.

R″ = Me, Et

24.

26.

27.

R″″ = H, Me, Et or

R″″ and R″″ together form a C3-C6 ring

-continued

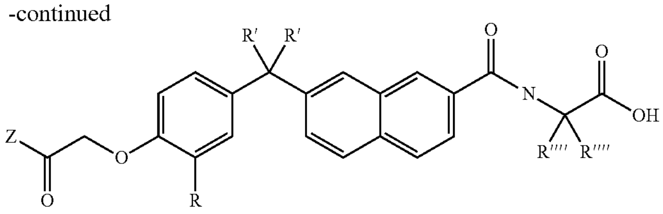

27.

R'''' = H, Me, Et or
R'''' and R'''' together form a C3-C6 ring

Scheme III.

Alcohol 17 is reacted with BF3-OEt2 and o-cresol (or another ortho substituted phenol) to give phenol 21. Phenol 21 is reacted with an alpha haloketone (z-C(O)$CH_2$hal, where z is an alkyl group or a substituted alkyl group) and a base to give ketone 22. Ketone 22 is treated with a hindered base (LDA or NaHMDS) and either methyl halide or ethyl halide (or other alkyl halide) to afford ketone 23. Ketone 23 is reacted with an alkali hydroxide to give acid 24. Acid 24 is coupled with substituted amino acid ester using EDCI/HOBT/NMM (N-methylmorpholine) to amide-ester 26. Coupling of acid 24 with cyclic amino acid ester the corresponding cyclic amide-ester 26 is obtained. Amide-ester 26 is reacted with alkali hydroxide to give amide 27.

Scheme IV

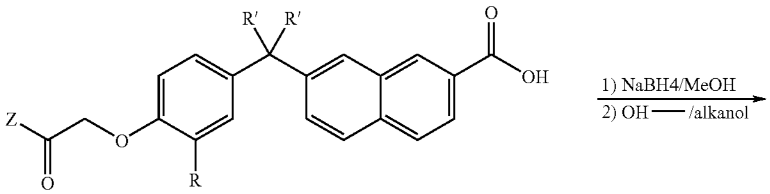

24.
R = C1-C3 alkyl

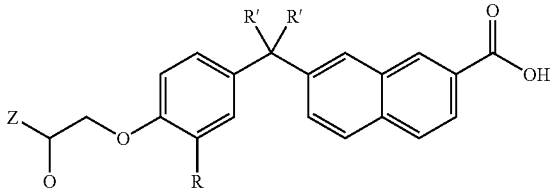

28.
R = C1-C3 alkyl

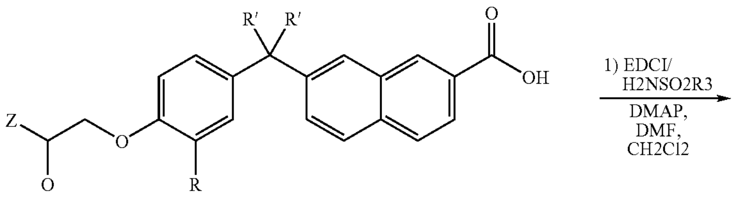

28.

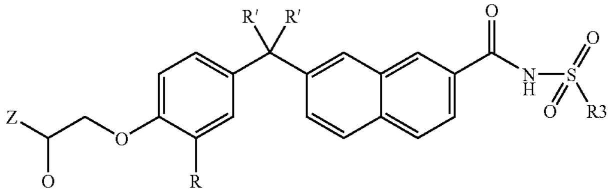

29.
R3 = C1-C6 alkyl

-continued
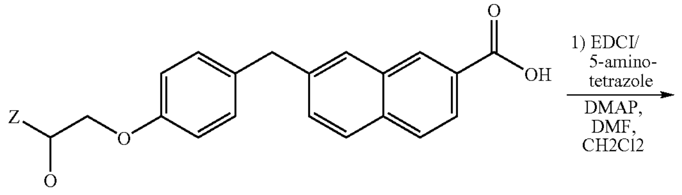
28.
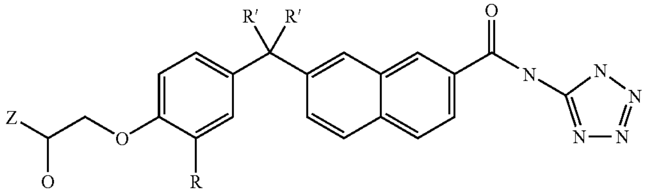
30.
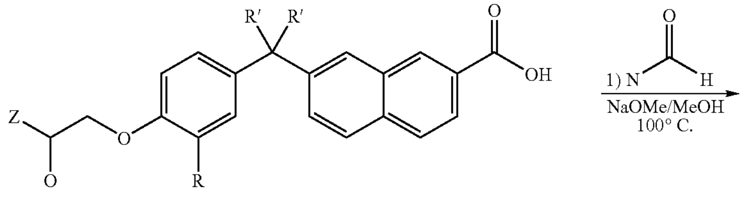
28.
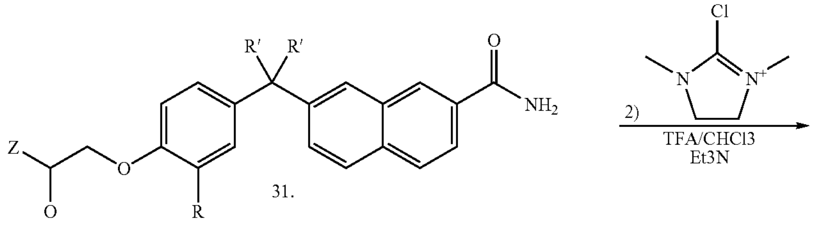
31.
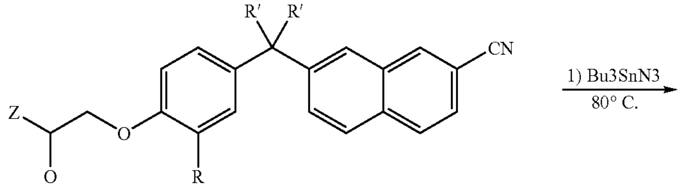
32.
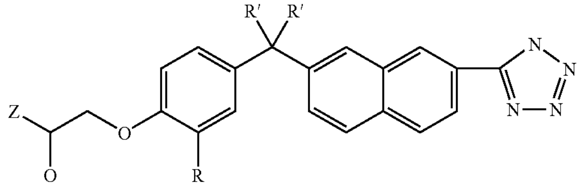
33.
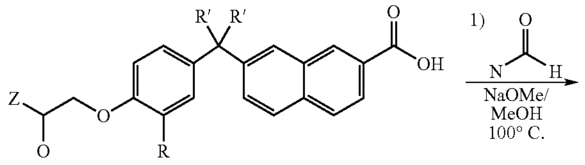
28.

-continued

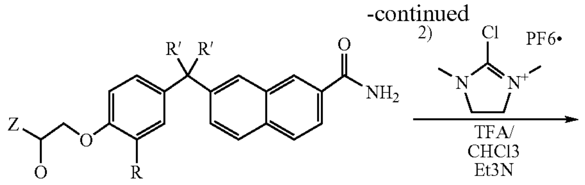

31.

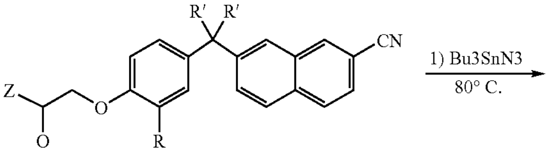

32.

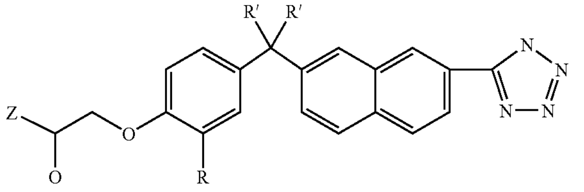

33.

Scheme IV.

Ketone-acid 24 is reacted with NaBH4/MeOH to give alcohol-acid 28. Alcohol-acid 28 is coupled with substituted sulfonamide using EDCI/DMAP to afford acylsulfonamide 29. Alcohol-acid 28 is reacted with EDCI/5-aminotetrazole/DMAP to give acylaminotetrazole 30. (The 5-aminotetrazole can be replaced with other heterocyclics or heteroaryl groups as desired.) Alcohol-acid 28 is reacted with formamide and NaOMe at 100° C. to produce amide 31. Amide 31 is reacted with Et3N, 2-chloro-1,3-dimethylimidazolinium hexafluorophosphate, and TFA to afford nitrile 32. Nitrile 32 is reacted with Bu3SnN3 at 80° C. to give tetrazole 33.

Example 1

Preparation of 6-{1-[4-(3,3-dimethyl-2-oxobutoxy)-3-methylphenyl]-1-ethylpropyl}naphthalene-2-carboxylic acid

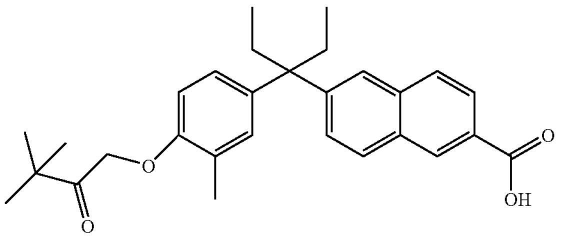

A. 6-Hydroxynaphthalene-2-carboxylic acid methyl ester

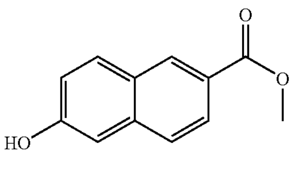

Treat a mixture of 6-hydroxy-2-naphthoic acid (4.45 g, 23.6 mmol) in 2,2-dimethoxypropane (235 mL) with conc. HCl (24 mL) and then MeOH (60 mL). Stir the reaction at RT for 16 h and then at 55° C. for 16 h. Pour the reaction mixture into EtOAc (250 mL) and wash with brine (3×100 mL). Dry the organic layer over Na2SO4, concentrate the filtrate, and chromatograph the concentrated filtrate (0.5 kg silica gel, 5:95 to 15:85 EtOAc:hex) to give the title compound (4.77 g, quant). MS (ES) m/e 203 (M+1).

B. 6-Benzyloxynaphthalene-2-carboxylic acid methyl ester

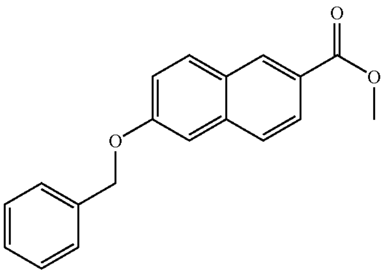

Treat 6-hydroxynaphthalene-2-carboxylic acid methyl ester (4.77 g, 23.6 μmmol) and benzyl bromide (3.3 mL, 28.3 mmol) in DMF (22 mL) with cesium carbonate (15.3 g, 47.2 mmol). Stir the mixture for 22 h at RT and concentrate. Dilute the concentrate with EtOAc (300 mL) and water (100 mL). Wash the organic layer with brine (3×100 mL), dry it over Na2SO4, and filter. Concentrate the filtrate. Purify the product using medium pressure silica gel chromatography (15:85 to 50:50 EtOAc:hex) to give the title compound as a white solid (5.75 g, 83%). MS (ES) m/e 293 (M+1).

C. 3-(6-Benzyloxynaphthalen-2-yl)pentan-3-ol

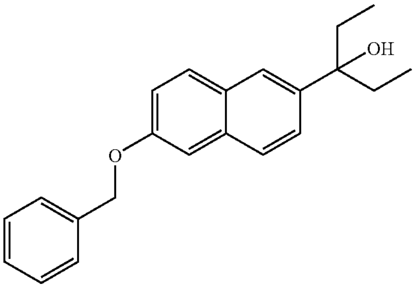

Cool 6-benzyloxynaphthalene-2-carboxylic acid methyl ester (5.75 g, 19.67 mmol) in THF (115 mL) to about 0° C. and treat the solution dropwise with ethyl magnesium bromide (23.0 mL, 69.0 mmol, 3.0 M in ether). Allow the reaction to warm to RT and stir it for 3 h. Quench with water and concentrate. Dissolve the crude residue in CH2CL2 (200 mL), wash twice with brine, dry over Na2SO4 and filter. Concentrate the filtrate to give the title compound as a yellow solid (6.0 g, 95%). MS (ES) m/e 321 (M+1).

D. 6-(1-Ethyl-1-hydroxypropyl)naphthalen-2-ol

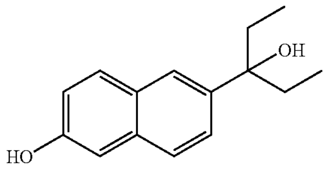

Treat a mixture of 3-(6-benzyloxynaphthalen-2-yl)pentan-3-ol (1.5 g, 4.68 mmol) and 5% PdlA12CO3 (0.90 g) in ethanol (750 mL) with hydrogen at 60 psi for 8 h at RT. Filter the catalyst from the reaction mixture and concentrate the filtrate to give the title compound as a yellow solid (0.94 g, 87%). MS (ES) m/e 229 (M−1).

E. Trifluoromethanesulfonic acid 6-(1-ethylpropenyl)naphthalen-2-yl ester

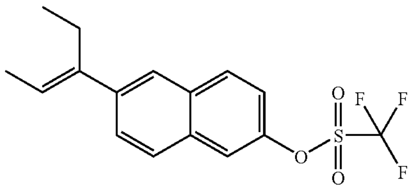

Cool a solution of 6-(1-ethyl-1-hydroxypropyl)naphthalen-2-ol (0.94 g, 4.08 mmol) and pyridine (1.3 mL, 16.3 mmol) in CH2CL2 (30 mL) in an ice bath and treat dropwise with trifluoromethanesulfonic anhydride (1.0 mL, 6.1 mmol). Remove the cooling bath, and stir the mixture at RT for 1 h. Quench the reaction mixture with ice water. Dilute the mixture with CH2CL2 (80 mL), wash twice with brine, dry over Na2SO4 and filter. Concentrate the filtrate and purify by silica gel radial chromatography (CH2CL2) to give the title compound as a yellow oil (0.93 g, 66%). MS (ES) m/e 361 (M+NH4).

F. 6-(1-Ethylpropenyl)naphthalene-2-carboxylic acid methyl ester

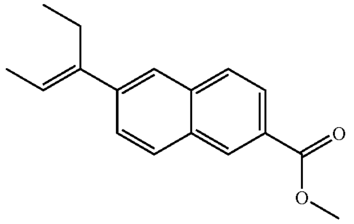

Treat a mixture containing trifluoromethanesulfonic acid 6-(1-ethylpropenyl)naphthalen-2-yl ester (0.92 g, 2.67 mmol), Pd(OAc)2 (0.020 mg, 0.09 mmol), bis-(diphenylphosphino)ferrocene (0.046 g, 0.083 mmol), Et3N (0.67 mL, 4.81 mmol), in MeOH (10 mL) and DMSO (15 mL) with carbon monoxide at 100 psi at 80° C. for 4 h. Pour the reaction mixture into ether (100 mL) and wash the mixture with brine (4×50 mL). Dilute the organic layer with EtOAc (100 mL), wash with brine, then dry over Na2SO4 and filter. Concentrate the filtrate to give the title compound as an off-white solid (0.67 g, quant). MS (ES) in/e 255 (M+1).

G. 6-[1-Ethyl-1-(4-hydroxy-3-methylphenyl)propyl]naphthalene-2-carboxylic acid methyl ester

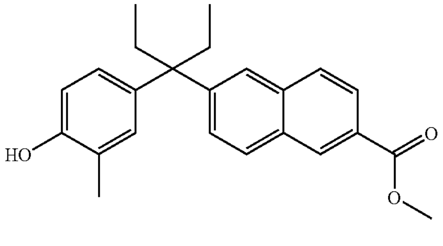

Cool a solution of 6-(1-ethyl-propenyl)naphthalene-2-carboxylic acid methyl ester (0.74 g, 2.75 mmol) and o-cresol (2.0 mL, 19.4 mmol) in CH2CL2 (20 mL) to −78° C.; dropwise add BF3-OEt2 (1.22 mL, 9.6 mmol). Remove the cooling bath and stir the reaction at RT for 16 h. Quench the reaction with ice water; then dilute with EtOAc (200 mL). Wash the resulting mixture twice with brine, dry over Na2SO4, filter, and concentrate the filtrate. Purify the product using medium pressure silica gel chromatography (100% hex to 25:75 EtOAc:hex) to give the title compound as a white solid (0.87 g, 87%). MS (ES) in/e 363 (M+1).

H. 6-{1-[4-(3,3-Dimethyl-2-oxobutoxy)-3-methylphenyl]-1-ethylpropyl}naphthalene-2-carboxylic acid methyl ester

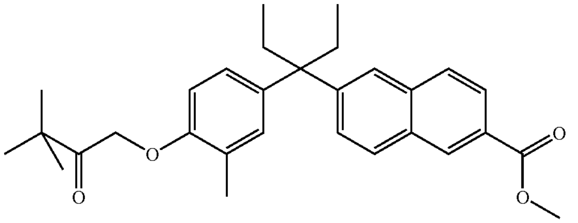

Stir a mixture containing 6-[1-ethyl-1-(4-hydroxy-3-methylphenyl)propyl]naphthalene-2-carboxylic acid methyl ester (0.87 g, 2.40 mmol), 1-bromopinacolone (0.64 g, 3.60 mmol), and potassium carbonate (1.0 g, 7.2 mmol) in acetone (15 mL) at RT for 16 h. Concentrate the reaction mixture and dilute the residue with EtOAc (100 mL) and water (50 mL). Adjust the pH of the mixture to 1 using 1 N HCl. Discard the aqueous layer and wash the organic layer with brine, dry over Na2SO4, then filter. Concentrate the filtrate and purify by silica gel radial chromatography (5:95 EtOAc:hex to 15:85 EtoAc:hex) to give the title compound as an off-white solid (0.53 g, 48%). MS (ES) m/e 461 (M+1).

I. 6-{1-[4-(3,3-Dimethyl-2-oxobutoxy)-3-methylphenyl]-1-ethylpropyl}naphthalene-2-carboxylic acid

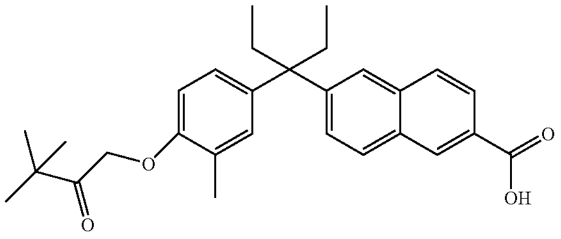

Treat a solution of 6-{1-[4-(3,3-Dimethyl-2-oxobutoxy)-3-methylphenyl]-1-ethylpropyl}-naphthalene-2-carboxylic acid methyl ester (0.53 g, 1.15 mmol) in THF (8 mL) and MeOH (16 mL) with 2N NaOH (2.9 mL, 5.8 mmol) and heat at 55° C. for 16 h. Concentrate the reaction mixture. Dilute the residue with in EtOAc (50 mL) and water (25 mL) and acidify the resulting mixture to pH 1 using 1N HCl. Discard the aqueous layer and wash the organic layer with brine, Dry the organic layer over Na2SO4, filter, and concentrate the filtrate to give the title compound as a yellow solid (0.45 g, 87%). MS (ES) m/e 447 (M+1).

Example 2

Preparation of 6-{1-Ethyl-1-[4-(2-hydroxy-3,3-dimethyl-butoxy)-3-methyl-phenyl]-propyl}-naphthalene-2-carboxylic acid

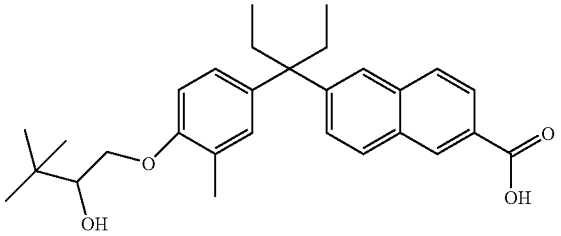

Treat a solution of 6-{1-[4-(3,3-dimethyl-2-oxobutoxy)-3-methylphenyl]-1-ethylpropyl}naphthalene-2-carboxylic acid (0.15 g, 0.34 mmol) in THF (6 mL) with NaBH4 (0.025 g, 0.67 mmol) and stir the reaction mixture at RT for 1 h. Quench the reaction first with water (5 mL) and then with 1N HCl (2 mL). Remove the THF under vacuum. Dilute the mixture with EtOAc (50 mL), wash with brine (2×), dry over NaSO4 and filter. Concentrate the filtrate to give the title compound (0.15 g). MS (ES) m/e 447 (M−1).

Example 2A and 2B

Preparation of enantiomers of 6-{1-Ethyl-1-[4-(2-hydroxy-3,3-dimethyl-butoxy)-3-methyl-phenyl]-propyl}-naphthalene-2-carboxylic acid

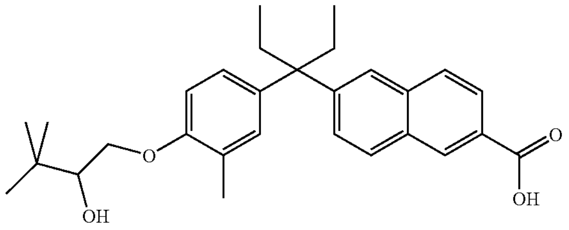

Chromatograph a mixture of racemic 6-{1-ethyl-1-[4-(2-hydroxy-3,3-dimethyl-butoxy)-3-methyl-phenyl]-propyl}-naphthalene-2-carboxylic acid (2.93 g) on a Chiralpak AD-H column, Daicel Chemical Industries, to give enantiomer 1, Example 2A (1.42 g, 48%) and enantiomer 2, Example 2B (1.38 g, 47%).

Enantiomer 1, Example 2A.

HPLC: ChiralPak AD-H (4.6×150); 60% heptane/40% IPA/0.1% TFA; 0.6 mL/m (flow rate); uv: 250 nm.

rt=10 m

Enantiomer 2, Example 2B

HPLC: ChiralPak AD-H (4.6×150); 60% heptane/40% IPA/0.1% TFA; 0.60 mL/m (flow rate); uv: 250 nm.

rt=16 m

Example 3

Preparation of [(6-{1-[4-(3,3-Dimethyl-2-oxo-butoxy)-3-methylphenyl]-1-ethylpropyl}naphthalene-2-carbonyl)amino]acetic acid

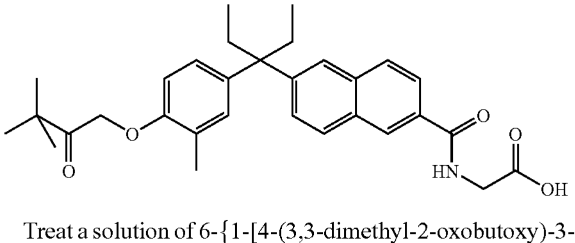

Treat a solution of 6-{1-[4-(3,3-dimethyl-2-oxobutoxy)-3-methylphenyl]-1-ethylpropyl}naphthalene-2-carboxylic acid (0.11 g, 0.246 mmol) in CH2CL2 (1.0 mL) dropwise with oxalyl chloride (0.13 mL, 1.48 mmol). Stir the solution at RT for 1 h and concentrate to give 6-{1-[4-(3,3-dimethyl-2-oxobutoxy)-3-methylphenyl]-1-ethylpropyl}naphthalene-2-carbonyl chloride ("the acid chloride"). Treat a mixture of methylglycine HCl (0.031 g, 0.25 mmol) and Et3N (0.51 mL, 0.37 mmol) in CH2CL2 (3 mL) with a solution of the acid chloride (0.057 g, 0.123 mmol) in CH2CL2 (1 mL). Stir the reaction at RT for 16 h and concentrate. Dissolve the residue in THF (0.5 mL) and MeOH (1.0 mL) and treat with 2N NaOH (0.24 mL, 0.48 mmol). Heat the solution to 50° C. for 16 h, concentrate, dilute with CH2CL2 and water (10 mL each). Acidify the resulting mixture to pH 1 using 5N HCl.

Wash the organic layer with brine, dry over Na2SO4, and filter. Concentrate the filtrate and purify by silica gel radial chromatography (10:90 MeOH:CH2CL2) to give the title compound as a white solid (0.021 g, 34%). MS (ES) m/e 504 (M+1).

Example 4

Preparation of 6-{1-[4-(3,3-dimethyl-2-oxobutoxy)-3-methylphenyl]-1-ethylpropyl}naphthalene-2-carboxylic acid dimethylamide

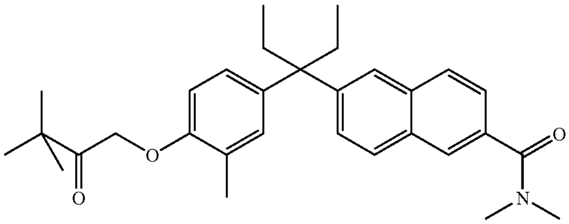

Treat a solution of dimethylamine (2.0 M in THF) (0.12 mL, 0.25 mmol) and Et3N (0.034 mL, 0.25 mmol) in CH2CL2 (3 mL) with 6-{1-[4-(3,3-dimethyl-2-oxobutoxy)-3-methylphenyl]-1-ethylpropyl}naphthalene-2-carbonyl chloride (0.057 g, 0.123 mmol) in CH2CL2 (1 mL). Stir the mixture at RT for 16 h; dilute with CH2CL2 and water. Acidify the resulting mixture to pH 1 using 5N HCl. Separate the organic layer from the aqueous layer. Wash the organic layer with brine, dry over Na2SO4, and filter. Concentrate the filtrate to give the title compound as a yellow solid (0.033 g, 57%). MS (ES) m/e 474 (M+1).

Example 5

Preparation of [(6-{1-[4-(3,3-Dimethyl-2-oxobutoxy)-3-methylphenyl]-1-ethylpropyl}naphthalene-2-carbonyl)methylamino]acetic acid

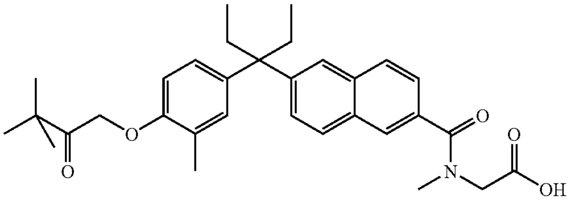

A. [(6-{1-[4-(3,3-Dimethyl-2-oxobutoxy)-3-methylphenyl]-1-ethylpropyl}naphthalene-2-carbonyl) methylamino]acetic acid ethyl ester

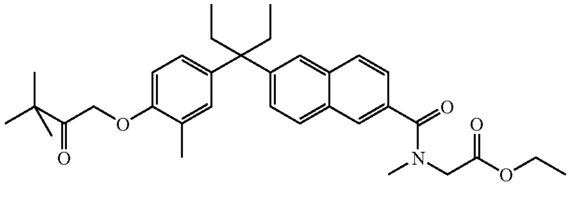

Dissolve 6-{1-[4-(3,3-dimethyl-2-oxobutoxy)-3-methylphenyl]-1-ethylpropyl}naphthalene-2-carboxylic acid (0.10 g, 0.222 mmol), sarcosine ethyl ester HCl (0.069 g, 0.45 mmol), DMAP (0.108 g, 0.89 mmol) and EEDC (0.086 g, 0.45 mmol) in CH2CL2 (2 mL). Stir the mixture at RT for 16 h. Dilute the reaction mixture with CH2CL2 and water. Acidify to pH 1 using 1N HCl. Separate and discard the aqueous layer. Wash the organic layer with brine, dry over Na2SO4, and filter. Concentrate the filtrate and purify by silica gel radial chromatography (25:75 EtOAc:hex to 50:50 EtoAc:hex) to give the title compound as a white solid (0.093 g, 78%). MS (ES) m/e 546 (M+1).

B. [(6-{1-[4-(3,3-Dimethyl-2-oxobutoxy)-3-methylphenyl]-1-ethylpropyl}naphthalene-2-carbonyl) methylamino]acetic acid Treat a solution of [(6-{1-[4-(3,3-Dimethyl-2-oxobutoxy)-3-methylphenyl]-1-ethylpropyl}naphthalene-2-carbonyl) methylamino]acetic acid ethyl ester (0.090 g, 0.16 mmol) in THF (1.25 mL) and EtOH (2.5 mL) with 2N NaOH (0.80 mL, 1.6 mmol). Heat the mixture to 50° C. for 16 h. Acidify the reaction mixture to pH 1 using 1N HCl. Concentrate the resulting mixture. Dilute the residue with EtOAc and water (25 mL each). Separate and discard the aqueous layer. Wash the organic layer with brine, dry over Na2SO4, and filter. Concentrated the filtrate to give the title compound as a white solid (0.070 g, 85%). MS (ES) m/e 518 (M+1).

Example 6

Preparation of 7-{1-[4-(3,3-Dimethyl-2-oxobutoxy)-3-methylphenyl]-1-ethylpropyl}naphthalene-2-carboxylic acid

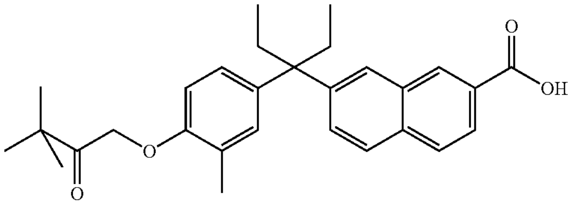

A. Trifluoromethanesulfonic acid 7-(1-ethyl-1-hydroxypropyl)naphthalen-2-yl ester

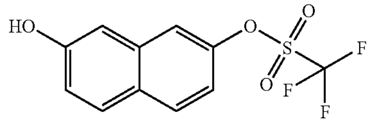

Cool a solution of 2,7-dihydroxynaphthalene (2.7 g, 31.2 mmol) and pyridine (4.53 mL, 56.0 mmol) in CH2CL2 (100 mL) in an ice bath and treat the cooled solution with trifluoromethanesulfonic anhydride (6.62 mL, 39.3 mmol). Remove the cooling bath and stir the mixture at RT for 2.5 h. Quench the reaction with ice water and dilute with CH2CL2 (200 mL). Wash the residue with water (2×100 mL) and then acidify to pH 3 using 1N HCl. Dry the organic layer over Na2SO4, filter and concentrate the filtrate. Purify the product by medium pressure silica gel chromatography (10:90 EtOAc:hex to 25:75 EtOAc:hex) to give the title compound as a yellow oil (4.1 g, 45%). MS (ES) m/e 291 (M+1).

B. 7-Hydroxynaphthalene-2-carboxylic acid methyl ester

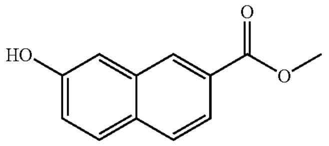

Treat a mixture containing trifluoromethanesulfonic acid 7-(1-ethyl-1-hydroxypropyl)naphthalen-2-yl ester (0.41 g, 14.1 mmol), Pd(OAc)2 (0.30 g, 1.38 mmol), bis-(diphenylphosphino)ferrocene (0.705 g, 1.27 mmol), Et3N (10.2 mL, 73.2 mmol), in MeOH (12 mL) and DMSO (18 mL) with carbon monoxide at 100 psi at 80° C. for 4 h. Pour the reaction mixture into ether (300 mL) and wash with brine (5×100 mL). Add EtOAc (250 mL), wash the organic layer with brine, dry over Na2SO4, and filter. Concentrate the filtrate to give the title compound as a tan solid (2.84 g, quant). $^{1}$H NMR (400 MHz, $CDCl_3$) δ 3.98 (s, 3H), 7.23-7.29 (m, 2H), 7.78 (t, J=8.3 Hz, 2H), 7.88-7.90 (m, 1H), 8.43 (d, J=0.88 Hz, 1H).

C. 7-Benzyloxynaphthalene-2-carboxylic acid methyl ester

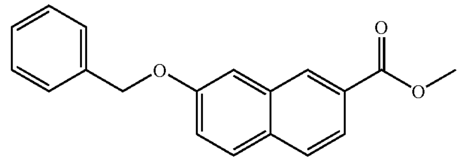

Treat a solution of 7-hydroxynaphthalene-2-carboxylic acid methyl ester (2.84 g, 14.0 mmol) and benzyl bromide (1.84 mL, 15.5 mmol in DMF (14 mL) with cesium carbonate (9.10 g, 27.9 mmol). Stir the mixture for 2 h and concentrate. Dissolve the crude residue in EtOAc (150 mL) and 1 N HCl (50 mL). Wash the organic layer with brine (3×100 mL), dry over Na2SO4, and filter. Concentrate the filtrate and purify using medium pressure silica gel chromatography (10:90 EtOAc:hex) to give the title compound as a white solid (1.47 g, 36%). MS (ES) m/e 293 (M+1).

D. 3-(7-Benzyloxynaphthalen-2-yl)pentan-3-ol

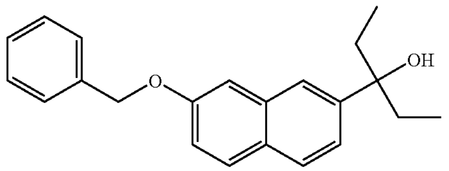

Cool a THF (30 mL) solution of 7-benzyloxynaphthalene-2-carboxylic acid methyl ester (1.47 g, 5.03 mmol) with an ice bath and treat the cooled solution dropwise with ethyl magnesium bromide (5.9 mL, 17.6 mmol, 3.0M in ether). Remove the ice bath and stir the reaction for 3 h. Quench the reaction with ice water, then treat with 1 N HCl, and concentrate to provide a crude product. Dissolve the crude product in EtOAc (100 mL). Wash the organic layer twice with brine, dry over Na2SO4, and filter. Concentrate the filtrate and purify using radial silica gel chromatography (5:95 to 15:85 EtOAc: hex) to give a yellow solid (01.46 g, 90%). $^{1}$H NMR (400 MHz, $CDCl_3$) δ0.787 (t, J=7.5 Hz, 6H), 1.67 (br s, 1H), 1.82-2.02 (m, 4H), 5.19 (s, 2H), 7.19-7.44 (m, 6H), 7.50 (d, J=6.6 Hz, 2H), 7.73 (d, J=8.8 Hz, 2H), 7.77 (d, J=1.8 Hz, 1H).

E. 7-(1-Ethyl-1-hydroxypropyl)naphthalen-2-ol

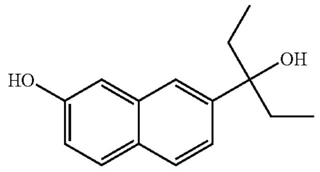

Treat a mixture of 3-(7-benzyloxynaphthalen-2-yl)pentan-3-ol (1.45 g, 4.53 mmol) and 5% Pd/Al2CO3 (0.044 g) in EtOH (725 mL) with hydrogen at 60 psi for 8 h at RT. Remove the catalyst by filtration and concentrate the filtrate to give the title compound as a yellow oil (0.98 g, 94%). MS (ES) m/e 229 (M−1).

F. Trifluoromethanesulfonic acid 7-(1-ethyl-1-hydroxypropyl)naphthalen-2-yl ester

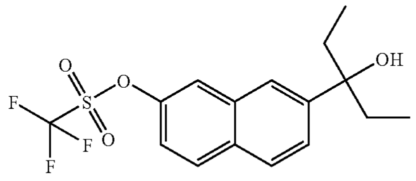

Cool a CH2CL2 (30 mL) solution of 7-(1-ethyl-11-hydroxypropyl)naphthalen-2-ol (0.97 g, 4.2 mmol) and pyridine (1.3 mL, 16.3 mmol) with an ice bath. Treat the cooled solution dropwise with trifluoromethanesulfonic anhydride (1.0 mL, 6.1 mmol). Remove the cooling bath and stir the mixture for 1.5 h at RT. Quench the reaction with ice water. Dilute the reaction mixture with EtOAc and water (100 mL each) and acidify to pH 1 using 0.1N HCl. Dry the organic layer over Na2SO4, filter and concentrate the filtrate. Purify by radial silica gel (2:98 to 10:90 EtOAc:hex) to give the title compound as a colorless oil (1.46 g, 66%). MS (ES) m/e 377 (M-NH4).

G. 7-(1-Ethyl-1-hydroxypropyl)naphthalene-2-carboxylic acid methyl ester

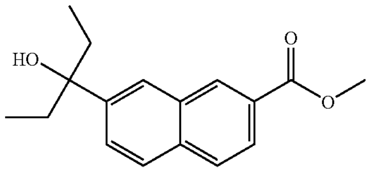

Treat a mixture of trifluoromethanesulfonic acid 7-(1-ethyl-1-hydroxypropyl)naphthalen-2-yl ester (1.0 g, 2.76 mmol), Pd(OAc)2 (0.062 g, 0.27 mmol), bis-(diphenylphosphino)ferrocene (0.14 g, 0.25 mmol), Et3N (2.0 mL, 14.3 mmol) in MeOH (10 mL) and DMSO (15 mL) with carbon monoxide at 100 psi at 80° C. for 4 h. Pour the reaction mixture into ether (100 mL) and wash the resulting solution with brine (4×50 mL). Add EtOAc (100 mL), wash the organic layer with brine. Dry the organic layer over Na2SO4, filter, and concentrate the filtrate. Purify by silica gel radial chromatography (5:95 to 15:85 EtOAc:hex) to give the title compound as a yellow oil (0.71 g, 94%). $^{1}$H NMR (400 MHz, $CDCl_3$) δ 0.792 (t, J=7.5 Hz, 6H), 1.80-2.04 (m, 4H), 4.00 (s, 3H), 7.58 (dd, J=8.8, 1.4 Hz, 1H), 7.80-7.87 (m, 2H), 7.99 (d, J=1.3 Hz, 1H), 8.02 (d, J=1.8 Hz, 1H), 8.05 (d, J=1.8 Hz, 1H), 8.61 (d, J=1.0 Hz, 1H).

H. 7-[1-Ethyl-1-(4-hydroxy-3-methylphenyl)propyl] naphthalene-2-carboxylic acid methyl ester

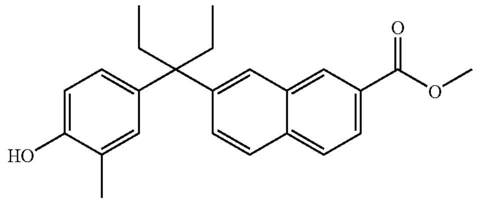

Cool a CH2CL2 (20 mL) solution of 7-(1-ethyl-1-hydroxypropyl)naphthalene-2-carboxylic acid methyl ester (0.73 g, 2.68 mmol) and o-cresol (1.54 mL, 15.0 mmol) to −78° C.; then dropwise add BF3-OEt2 (0.76 mL, 6.0 mmol). Allow the reaction mixture to warm to RT and stir for 1 h. Quench the reaction with ice water. Dilute the resulting mixture with EtOAc (200 mL). Wash the mixture with brine, dry the organic layer over Na2SO4, filter and concentrate the filtrate. Purify by silica gel radial chromatography (5:95 to 35:65 EtOAc:hex) to give the title compound as a yellow oil (0.93 g, 86%). MS (ES) m/e 363 (M+1).

I. 7-{1'-[4-(3,3-Dimethyl-2-oxobutoxy)-3-methylphenyl]-1-ethylpropyl}naphthalene-2-carboxylic acid methyl ester

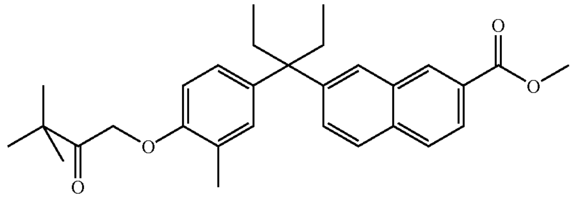

Stir a mixture of 7-[1-ethyl-1-(4-hydroxy-3-methylphenyl)propyl]naphthalene-2-carboxylic acid methyl ester (0.87 g, 2.40 mmol), 1-bromopinacolone (1.54 g, 8.68 mmol), and potassium carbonate (2.4 g, 17.4 mmol) in acetone (20 mL) for 4 h at RT. Concentrate the reaction mixture and then dilute the residue with EtOAc (100 mL) and water (50 mL). Adjust the pH of the mixture to 1 using 1 N HCl. Discard the aqueous layer. Wash the organic layer with brine, dry over Na2SO4 and filter. Concentrate the filtrate and purified by silica gel radial chromatography (5:95 EtOAc:hex to 15:85 EtoAc:hex) to give the title compound as a white solid (1.1 g, 82%). MS (ES) m/e 461 (M+1).

J. 7-{1-[4-(3,3-Dimethyl-2-oxobutoxy)-3-methylphenyl]-1-ethylpropyl}naphthalene-2-carboxylic acid

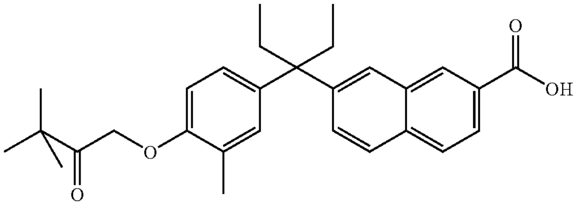

Treat 7-{1-[4-(3,3-dimethyl-2-oxobutoxy)-3-methylphenyl]-1-ethylpropyl}naphthalene-2-carboxylic acid methyl ester (1.1 g, 2.4 mmol) in THF (15 mL) and MeOH (30 mL) with 2N NaOH (6.0 mL, 12.0 mmol) and heat to 55° C. for 16 h. Then concentrate the reaction mixture and dilute the residue with CH2CL2 and water (50 mL each). Acidify the mixture to pH 1 using 1N HCl. Discard the aqueous layer and wash the organic layer with brine. Dry the organic layer over Na2SO4, filter and concentrate the filtrate. Purify by silica gel radial chromatography (2:98 MeOH:CH2CL2 to 10:90 MeOH:CH2CL2) to give the title compound as a yellow solid (0.96 g, 90%). MS (ES) m/e 447 (M+1).

Example 7

Diastereomeric isomer pair 1 of 2-[6-{1-ethyl-1-[4-(1-ethyl-2-hydroxy-3,3-dimethyl-butoxy)-3-methyl-phenyl]-propyl}-naphthalene-2-carbonylamino]acetic acid

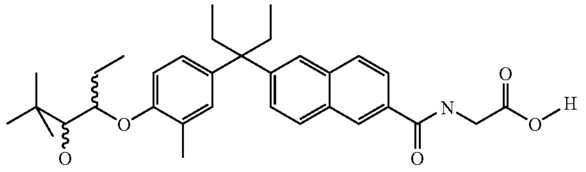

A. 4-Bromo-2,2-dimethylhexane-3-one

Slowly add bromine (10.87 ml, 212.15 mmol) to 2,2-dimethylhexane-3-one (27.20 g, 212.15 mmol) in ether (200 ml) and allow the reaction to stir for 14 h. Combine the reaction mixture with water (200 ml) and partition. Dry the organic layer over Na2SO4, filter and then concentrate the filtrate to provide the title compound as a yellow oil (48.2 g, quant). [1]NMR (400 MHz, $CDCl_3$) δ ppm: 1.01 (t, J=7.6 Hz, 3H), 1.27 (s, 9H), 2.03 (m, 2H), 4.58 (t, J=7.2 Hz, 1H). High Res. ES-MS: 207.0348; calc. for $C_8H_{15}BrO$+H, 207.0384.

B. 6-{1-[4-(3,3-Dimethyl-1-ethyl-2-oxobutoxy)-3-methylphenyl]1-ethylpropyl}naphthalene-2-carboxylic acid methyl ester

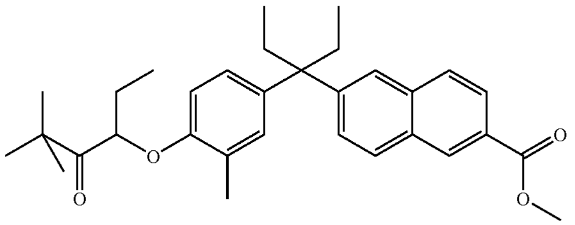

Add 4-bromo-2,2-dimethylhexane-3-one (660 mg, 3.187 mmol) to a mixture of 6-[1-ethyl-1-(4-hydroxy-3-methylphenyl)propyl]naphthalene-2-carboxylic acid methyl ester (1.1 g, 3.035 mmol), and K2CO3 (629 mg, 4.55 mmol) in DMF (10 ml). Maintain the reaction mixture 45° C. for 14 h. Add an additional amount of 4-bromo-2,2-dimethylhexane-3-one (314 mg, 1.52 mmol) and maintain the mixture at 60° C. while stirring for 62 h. Cool the reaction mixture and dilute it with CH2Cl2, filter, and concentrate in vacuo. Chromatograph the resulting residue (CH2Cl2to 1% EtOAc/CH2Cl2) to give the title compound as a colorless viscous oil (1.299 g, 88%). [1]NMR (400 MHz, $CDCl_3$) δ ppm: 0.62 (t, J=7.2 Hz, 6H), 1.01 (t, J=7.6 Hz, 3H), 1.16 (s, 9H), 1.88 (m, 2H), 2.16 (m, 4H), 2.19 (s, 3H), 3.97 (s, 3H), 4.86 (dd, J=5.2, 1.6 Hz, 1H), 6.53 (d, J=8.4 Hz, 1H), 6.88 (m, 2H), 7.14 (dd, J=7.2, 1.6 Hz, 1H), 7.73 (d, J=8.8 Hz, 1H), 7.82 (s, 1H), 7.85 (d, J=8.8 Hz, 1H), 8.04 (dd, J=6.4, 2.0 Hz, 1H), 8.52 (s, 1H). High Res. ES-MS: 511.2824; calc. for $C_{32}H_{40}O_4$+Na: 511.2825.

C. Diastereomeric isomer pair 1 and diastereomeric isomer pair 2 of 6-{1-Ethyl-1-[4-(1-ethyl-2-hydroxy-3,3-dimethyl-butoxy)-3-methyl-phenyl]-propyl}-naphthalene-2-carboxylic acid methyl ester

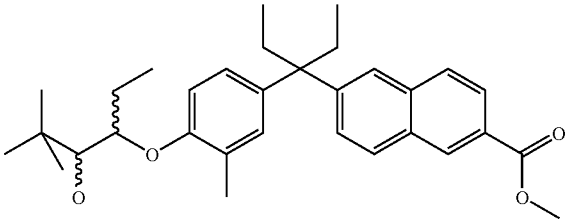

Following the procedure described in Example 2; treat 6-{1-[4-(3,3-dimethyl-1-ethyl-2-oxobutoxy)-3-methylphenyl]-1-ethylpropyl}naphthalene-2-carboxylic acid methyl ester with NaBH4 in THF at 0 C. Chromatograph the residue (CH2Cl2 to 2% EtOAc/CH2Cl2) to give diastereomeric isomer pair 1 of the title compound as a glassy foam (1.004 g, 77%) and diastereomeric isomer pair 2 of the title compound as a glassy foam (102 mg, 8%).

Diastereomeric isomer pair 1: $^1$NMR (400 MHz, $CDCl_3$) δ ppm: 0.64 (t, J=7.6 Hz, 6H), 0.93 (t, J=8.0 Hz, 3H), 0.93 (s, 9H), 1.70 (m, 1H), 1.81 (m, 1H), 2.12 (s, 3H), 2.17 (m, 4H), 2.61 (bs, 1H), 3.27 (s, 1H), 3.97 (s, 3H), 4.27 (dd, J=5.6, 3.6 Hz, 1H), 6.63 (d, J=8.8 Hz, 1H), 6.90 (s, 1H), 6.93 (d, J=8.4 Hz, 1H), 7.18 (d, J=8.8 Hz, 1H), 7.75 (d, J=8.8 Hz, 1H), 7.83 (s, 1H), 7.86 (d, J=8.4 Hz, 1H), 8.04 (dd, J=7.2, 1.2 Hz, 1H), 8.52 (s, 1H). High Res. ES-MS: 513.2914; calc. for $C_{32}H_{42}O_4$+Na: 513.2981.

Analysis for $C_{32}H_{42}O_4$; Calcd: C, 78.33; H, 8.63; N, 0.00. Found: C, 78.21; H, 8.75; N, 0.11.

Diastereomeric Isomer Pair 2:

$^1$NMR (400 MHz, $CDCl_3$) δ ppm: 0.64 (t, J=7.2 Hz, 6H), 0.99 (t, J=4.4 Hz, 3H), 0.99 (s, 9H), 1.81 (m, 2H), 2.12 (s, 3H), 2.16 (m, 4H), 3.59 (d, J=4.0 Hz, 1H), 3.97 (s, 3H), 4.35 (m, 1H), 6.67 (d, J=8.4 Hz, 1H), 6.91 (m, 2H), 7.18 (dd, J=6.8, 2.0 Hz, 1H), 7.75 (d, J=8.8 Hz, 1H), 7.83 (s, 1H), 7.86 (d, J=8.8 Hz, 1H), 8.05 (dd, J=6.8, 2.2 Hz, 1H), 8.52 (s, 1H). High Res. ES-MS: 513.2973; calc. for $C_{32}H_{42}O_4$+Na: 513.2981.

D. Diastereomeric isomer pair 1 of 6-{1-ethyl-1-[4-(1-ethyl-2-hydroxy-3,3-dimethyl-butoxy)-3-methyl-phenyl]-propyl}-naphthalene-2-carboxylic acid

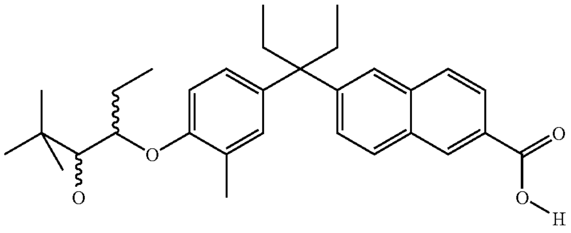

Add KOH (321 mg, 5.724 mmol) to a mixture of diastereomeric isomer pair 1 of 6-{1-ethyl-1-[4-(1-ethyl-2-hydroxy-3,3-dimethyl-butoxy)-3-methyl-phenyl]propyl}-naphthalene-2-carboxylic acid methyl ester (702 mg, 1.431 mmol), THF (9 ml), MeOH (3 ml), and H2O (1 ml). Heat the reaction mixture to 60° C. and stir it for 14 h. Cool and partition the reaction mixture between Et2O and 1N HCl. Dry the organic layer over MgSO4, filter, and concentrate the filter in vacuo to give the title compound as a glassy solid (665 mg, 97%). $^1$NMR (400 MHz, $CDCl_3$) δ ppm: 0.64 (t, J=7.6 Hz, 6H), 0.93 (t, J=8.4 Hz, 3H), 0.93 (s, 9H), 1.72 (m, 1H), 1.82 (m, 1H), 2.12 (s, 3H), 2.19 (q, 4H), 3.28 (s, 1H), 4.28 (dd, J=6.0, 3.2 Hz, 1H), 6.65 (d, J=8.4 Hz, 1H), 6.90 (d, J=2.0 Hz, 1H), 6.94 (dd, J=6.0, 2.4 Hz, 1H), 7.21 (dd, J=7.2, 1.6 Hz, 1H), 7.78 (d, J=8.8 Hz, 1H), 7.86 (s, 1H), 7.89 (d, J=8.8 Hz, 1H), 8.09 (dd, J=6.8, 1.6 Hz, 1H), 8.62 (s, 1H). High Res. ES-MS: 499.2832; calc. for $C_{31}H_{40}O_4$+Na: 499.2825.

Analysis for $C_{31}H_{40}O_4$; Calcd: C, 78.11; H, 8.46; N, 0.00. Found: C, 78.03; H, 8.59; N, 0.12.

E. Diastereomeric isomer pair 1 of 6-{1-ethyl-1-[4-(1-ethyl-2-hydroxy-3,3-dimethyl-butoxy)-3-methyl-phenyl]-propyl}-naphthalene-2-carbonylaminoacetic acid methyl ester

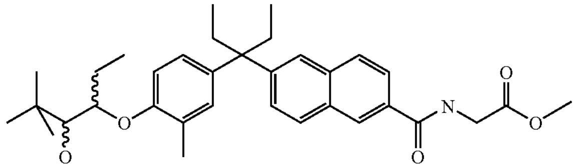

Add glycine methyl ester hydrochloride (95 mg, 0.755 mmol), HOBT (102 mg, 0.755 mmol), EDCI (206 mg, 1.08 mmol), and Et3N (0.4 ml, 0.726 mmol) to diastereomeric isomer pair 1 of 6-{1-ethyl-1-[4-(1-ethyl-2-hydroxy-3,3-dimethyl-butoxy)-3-methyl-phenyl]-propyl}-naphthalene-2-carboxylic acid (343 mg, 0.72 mmol) and CH2Cl2 (5 ml). Stir the reaction for 14 h. Concentrate the reaction mixture in vacuo, and chromatograph the residue (CH2Cl2 to 15% EtOAc/CH2Cl2) to give the title compound as a colorless foam (373 mg, 95%). $^1$NMR (400 MHz, $CDCl_3$) δ ppm: 0.64 (t, J=7.6 Hz, 6H), 0.93 (t, J=8.4 Hz, 3H), 0.93 (s, 9H), 1.68 (m, 1H), 1.81 (m, 1H), 2.12 (s, 3H), 2.18 (q, 4H), 2.60 (bs, 1H), 3.27 (s, 1H), 3.83 (s, 3H), 4.27 (dd, J=5.6, 3.2 Hz, 1H), 4.31 (d, J=5.2 Hz, 2H), 6.63 (d, J=8.0 Hz, 1H), 6.75 (t, J=4.8 Hz, 1H), 6.89 (d, J=2.4 Hz, 1H), 6.93 (dd, J=6.4, 2.0 Hz, 1H), 7.18 (dd, J=6.8, 2.0 Hz, 1H), 7.75 (d, J=8.4 Hz, 1H), 7.83 (d, J=2.0, 1H), 7.86 (m, 2H), 8.26 (s, 1H). High Res. ES-MS: 570.3116; calc. for $C_{34}H_{45}NO_5$+Na: 570.3196.

Analysis for $C_{34}H_{45}NO_5$; Calcd: C, 74.56; H, 8.28; N, 2.56. Found: C, 74.28; H, 8.23; N, 2.68.

F. Diastereomeric isomer pair 1 of 2-[6-{1-ethyl-1-[4-(1-ethyl-2-hydroxy-3,3-dimethyl-butoxy)-3-methyl-phenyl]-propyl}-naphthalene-2-carbonylamino]acetic acid

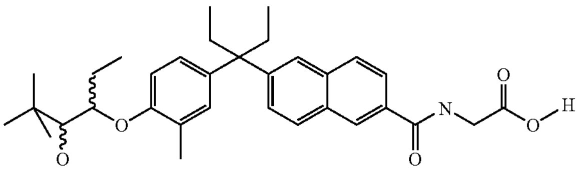

Add 2.5 M LiOH/H2O (0.82 ml, 2.04 mmol) to diastereomeric isomer pair 1 of 2-[6-{1-ethyl-1-[4-(1-ethyl-2-hydroxy-3,3-dimethyl-butoxy)-3-methyl-phenyl]-propyl}-naphthalene-2-carbonylamino]acetic acid methyl ester (373 mg, 0.681 mmol) in THF (3 ml), and MeOH (1.5 ml). Stir the reaction for 14 h; then partition the reaction mixture between Et2O and 1N HCl. Dry the organic layer with MgSO4, concentrate and triturate the residue with CH2Cl2/MeOH/hexanes to give the title compound as a white solid (310 mg, 85%). $^1$NMR (400 MHz, $CDCl_3$) δ ppm: 0.64 (t, J=7.2 Hz, 6H), 0.93 (t, J=8.0 Hz, 3H), 0.93 (s, 9H), 1.68 (m, 1H), 1.81 (m, 1H), 2.11 (s, 3H), 2.15 (q, 4H), 3.28 (s, 1H), 4.27 (dd, J=5.2, 3.6 Hz, 1H), 4.35 (d, J=4.8 Hz, 2H), 6.63 (d, J=8.0 Hz, 1H), 6.83 (t, J=4.8 Hz, 1H), 6.89 (s, 1H), 6.93 (dd, J=6.4, 2.2 Hz, 1H), 7.18 (dd, J=7.2, 1.6 Hz, 1H), 7.74 (d, J=8.8 Hz, 1H), 7.88 (m, 3H), 8.27 (s, 1H). High Res. ES-MS: 556.3046; calc. for $C_{33}H_{43}NO_5$+Na: 556.3040.

Example 8

Preparation of diastereomeric isomer pair 1 of N-methyl-2-[6-{1-ethyl-1-[4-(1-ethyl-2-hydroxy-3,3-dimethyl-butoxy)-3-methyl-phenyl]-propyl}-naphthalene-2-carbonyl-amino]acetic acid

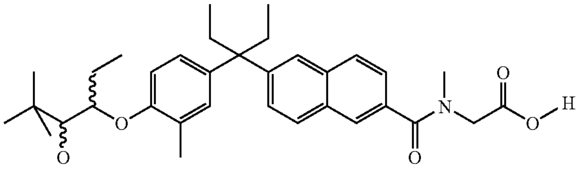

A. Diastereomeric isomer pair 1 of N-methyl-2-[6-{1-ethyl-1-[4-(1-ethyl-2-hydroxy-3,3-dimethyl-butoxy)-3-methyl-phenyl]-propyl}-naphthalene-2-carbonyl-amino]acetic acid ethyl ester

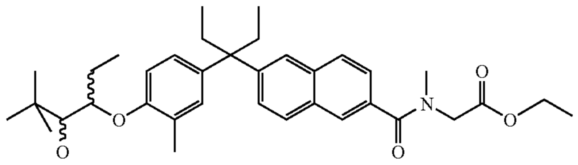

Following a procedure analogous to Example 7E esterify the diastereomeric isomer pair 1 of 6-{1-ethyl-1-[4-(1-ethyl-2-hydroxy-3,3-dimethyl-butoxy)-3-methyl-phenyl]-propyl}-naphthalene-2-carboxylic acid using N-methyl glycine ethyl ester hydrochloride to provide the title compound as a white foam (315 mg, 88%). $^1$NMR (400 MHz, $CDCl_3$) δ ppm: 0.64 (t, J=7.2 Hz, 6H), 0.93 (t, J=8.4 Hz, 3H), 0.93 (s, 9H), 1.31 (m, 3H), 1.68 (m, 1H), 1.80 (m, 1H), 2.12 (s, 3H), 2.17 (q, 4H), 2.60 (bs, 1H), 3.11 (s, 2H), 3.16 (s, 1H), 3.27 (s, 1H), 4.05 (s, 0.73H), 4.27 (m, 3H), 4.32 (s, 1.27H), 6.63 (d, J=8.8 Hz, 1H), 6.90 (s, 1H), 6.93 (d, J=8.8 Hz, 1H), 7.16 (d, J=10.0 Hz, 1H), 7.49 (m, 1H), 7.55 (d, J=7.6 Hz, 1H), 7.68 (m, 1H), 7.81 (s, 1H), 7.87 (m, 2H). High Res. ES-MS: 598.3488; calc. for $C_{36}H_{49}NO_5$+Na: 598.3509. Analysis for $C_{36}H_{49}NO_5$; Calcd: C, 75.10; H, 8.58; N, 2.43. Found: C, 75.04; H, 8.58; N, 2.43.

B. Diastereomeric isomer pair 1 of N-methyl-2-[6-{1-ethyl-1-[4-(1-ethyl-2-hydroxy-3,3-dimethyl-butoxy)-3-methyl-phenyl]-propyl}-naphthalene-2-carbonyl-amino]acetic acid ethyl ester

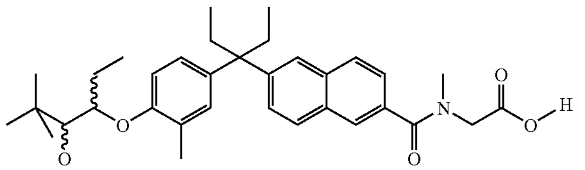

Following a procedure analogous to Example 7F, esterify the diastereomeric isomer pair 1 of N-methyl-2-[6-{1-ethyl-1-[4-(1-ethyl-2-hydroxy-3,3-dimethyl-butoxy)-3-methyl-phenyl]-propyl}-naphthalene-2-carbonyl-amino]acetic acid ethyl ester in THF and EtOH to give the title compound as a white solid (300 mg, quant.). $^1$NMR (400 MHz, $CDCl_3$) δ ppm: 0.64 (t, J=7.2 Hz, 6H), 0.93 (t, J=7.6 Hz, 3H), 0.93 (s, 9H), 1.65 (m, 1H), 1.83 (m, 1H), 2.12 (s, 3H), 2.15 (q, 4H), 3.16 (s, 3H), 3.28 (s, 1H), 4.12 (bs, 0.5H), 4.26 (dd, J=5.2, 3.6 Hz, 1H), 4.36 (s, 1.25H), 6.63 (d, J=8.4 Hz, 1H), 6.90 (s, 1H), 6.93 (d, J=8.8 Hz, 1H), 7.17 (d, J=8.0 Hz, 1H), 7.53 (m, 1H), 7.68 (m, 1H), 7.82 (s, 1H), 7.87 (m, 1H), 7.93 (m, 1H). High Res. ES-MS: 570.3140; calc. for $C_{34}H_{45}NO_5$+Na: 570.3196.

Example 9

3'-[4-(2-hydroxy-3,3-dimethylbutoxy)-3-methylphenyl]-3'-[12-(t-butoxycarbonylamino)-napthaline] pentane

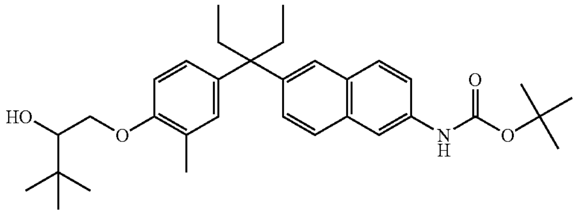

Treat 3'-[4-(2-Hydroxy-3,3-dimethyl-butoxy)-3-methyl-phenyl]-3' [(12-carboxylic acid)-naphthalene]pentane (1 eq.) in $CH_2CL_2$ with, Et3N (1.1 eq.) $(PhO)_2PO(N_3)$ (1.1 eq) and allow the reaction to stir for about 1 h Then concentrate the reaction mixture, and add the concentrated solution to a 90° C. solution of t-BuOH and heat with an open stream of nitrogen for about 1.75 h. Cool the reaction to RT, dissolve in a minimal of 1:1 $CH_2Cl_2$:10% EtOAc/Hex, and chromatographed (10% EtOAc/Hex) to give the title compound.

Example 10

3'-[4-(2-Hydroxy-3,3-dimethylbutoxy)-3-methylphenyl]-3'-[12-amino-napthaline]pentane

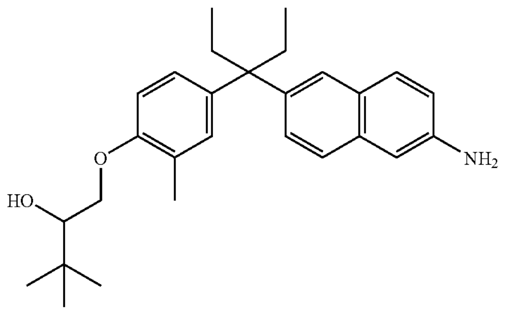

Treat mixture of 3'-[4-(2-hydroxy-3,3-dimethylbutoxy)-3-methylphenyl]-3'-[12-(t-butoxycarbonylamino)-napthaline] pentane (1 eq.), anisole (about 20 eq.) in $CH_2Cl_2$ (5 ml) with TFA (excess). Stir the reaction for about 2 h, concentrate, and partition the reaction mixture between EtOAc/satd $Na_2CO_3$. Wash the organic layer with water, dry over $Na_2SO_4$, and filter. Concentrate the filtrate and chromatograph the residue (50% $CHCl_3$/Hex to $CHCl_3$) to give the title compound.

Compounds of the Invention—Salts, Stereoisomers, & Prodrugs:

Salts of the compounds represented by Formula I are an additional aspect of the invention. The skilled artisan will also appreciate that the family of compounds of Formula I include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Sodium and potassium salts are particularly preferred. Salts are conveniently prepared from the free acid by treating the acid in solution with a base or by exposing the acid to an ion exchange resin. For example, a carboxylic acid substituent on the compound of Formula I may be selected as —$CO_2H$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.,* 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R— and S— isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:

CHIRALPAK AD, CHIRALPAK AS, CHIRALPAK OD, CHIRALPAK OJ, CHIRALPAK OA, CHIRALPAK OB, CHIRALPAK OC, CHIRALPAK OF, CHIRALPAK OG, CHIRALPAK OK, and CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Particularly preferred esters to use as prodrugs are; methyl, ethyl, propyl, isopropyl, n-butyl, isobutyl, morpholinoethyl, and N,N-diethylglycolamido.

N,N-diethylglycolamido ester prodrugs may be prepared by reaction of the sodium salt of a compound of Formula I (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula I (in a medium such as dimethylformamide) 4-(2-chloroethyl)morpholine hydrochloride (available from Aldrich Chemical Co., Milwaukee, Wis. USA, Item No. C5,220-3). For example, prodrugs may be prepared by reaction of the sodium salt for a compound of Formula I with;

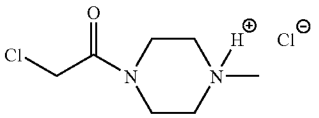

and sodium iodide to provide the ester prodrug pendent group

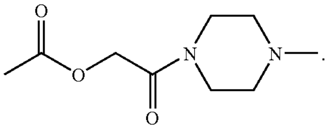

Also, lower alkyl (viz., $C_1$-$C_8$) ester prodrugs may be prepared by conventional means such as reacting the sodium or potassium salt (derived by forming the salt of any acidic compound of the invention; viz., reaction of a base such as KOH with an acidic group such as —$CO_2H$) of a compound of Formulae I with an alkyl iodide such as methyl iodide, ethyl iodide, n-propyl iodide, isopropyl iodide.

Pharmaceutical Formulations Containing the Novel Compounds of the Invention:

Pharmaceutical formulations of the invention are prepared by combining (e.g., mixing) a therapeutically effective amount of the compound of the invention (compounds of Formula I) together with a pharmaceutically acceptable carrier or diluent. The present pharmaceutical formulations are prepared by known procedures using well-known and readily available ingredients.

In making the compositions of the present invention, the compounds of the invention will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The compounds of the present invention are preferably formulated prior to administration.

The compounds of the invention may also be delivered by suitable formulations contained in a transderm patch. Alternatively, the compounds of the invention may be delivered to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active Ingredient. In tablets a compound of the invention is mixed with a carrier having the necessary binding properties in suitable proportions and compacted in the shape and size desired. The powders and tablets preferably contain from about 1 to about 99 weight percent of the compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient may be dissolved or suspended in a pharmaceutically acceptable carrier, such as sterile water, sterile organic solvent or a mixture of both. The compounds can often be dissolved in a suitable organic solvent, for instance aqueous propylene glycol. Other compositions can be made by dispersing the finely divided compounds of the invention in aqueous starch or sodium carboxymethyl cellulose solution or in a suitable oil.

Methods of Using the Compounds of the Invention:

Many disease states are benefited by treatment with the compounds of Formula I include, but are not limited to: disease states characterized by: abnormal calcium regulation, abnormal cell proliferation, abnormal cell differentiation, abnormal immune response, abnormal dermatological conditions, neurodegenerative condition, inflammation, vitamin D sensitivity, and/or hyperproliferative disorders.

Specific disease states benefited by treatment with one or more of the compounds of Formula I include, but are not limited to: Acne, Actinic keratosis, Alopecia, Alzheimer's disease, Benign prostatic hyperplasia, Bladder cancer, Bone maintenance in zero gravity, Bone fracture healing, Breast cancer, Chemoprevention of Cancer, Crohn's disease, Colon cancer, Type I diabetes, Host-graft rejection, Hypercalcemia, Type II diabetes, Leukemia, Multiple sclerosis, Myelodysplastic syndrome, Insufficient sebum secretion, Osteomalacia, Osteoporosis, Insufficient dermal firmness, Periodontal disease, Insufficient dermal hydration, Psoriatic arthritis, Prostate cancer, Psoriasis, Renal osteodystrophy, Rheumatoid arthritis, Scleroderma, Skin cancer, Systemic lupus, rythematosus, Skin cell damage from mustard vesicants, Ulcerative colitis, Vitiligo, and Wrinkles.

Particularly preferred is the treatment of psoriasis and/or osteoporosis by administration to a mammal (including a human) of a therapeutically effective amount of compounds of Formula I. By "pharmaceutically effective amount" it is meant that quantity of pharmaceutical agent corresponding to formulae I which prevents, removes or reduces the deleterious effects of a disease state in mammals, including humans.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably compounds of the invention or pharmaceutical formulations containing these compounds are in unit dosage form for administration to a mammal.

The unit dosage form can be a capsule or tablet itself, or the appropriate number of any of these. The quantity of Active Ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. Dosage will also depend on the route of administration. The compounds of the invention may be administered by a variety of routes including oral, aerosol, rectal, transdermal, sublingual, subcutaneous, intravenous, intramuscular, and intranasal. Particularly preferred is the treatment of psoriasis with an ointment type formulation containing the compounds of the invention. The ointment formulation may be applied as needed, typically from one to 6 times daily.

Treatment of psoriasis is preferably done with topical application by a formulation in the form of a cream, oil, emulsion, paste or ointment containing a therapeutically effective amount of a compound of the invention. The formulation for topical treatment contains from 0.5 to 0.00005 weight percent, preferably from 0.05 to 0.0005 weight percent, and most preferably from 0.025 to 0.001 of a Active Ingredient.

For example, two semisolid topical preparations useful as vehicles for VDR modulators in treatment and prevention of psoriasis are as follows:

Polyethylene Glycol Ointment USP (p. 2495)
Prepare Polyethylene Glycol Ointment as follows:

| | |
|---|---|
| Polyethylene Glycol 3350 | 400 g. |
| Polyethylene Glycol 400 | 600 g. |
| To make | 1000 g. |

Heat the two ingredients on a water bath to 65° C. Allow to cool, and stir until congealed. If a firmer preparation is desired, replace up to 100 g of the polyethylene glycol 400 with an equal amount of polyethylene glycol 3350.

| Hydrophilic Ointment USP (p. 1216) Prepare Hydrophilic Ointment as follows: | |
|---|---|
| Methylparaben | 0.25 g. |
| Propylparaben | 0.15 g. |
| Sodium Lauryl Sulfate | 10 g. |
| Propylene Glycol | 120 g. |
| Stearyl Alcohol | 250 g. |
| White Petrolatum | 250 g. |
| Purified Water | 370 g. |
| To make about | 1000 g. |

The Stearyl Alcohol and White Petrolatum are melted on a steam bath, and warmed to about 75° C. The other ingredients, previously dissolved in the water are added, warmed to 75° C., and the mixture stirred until it congeals.

For each of the above formulations the Active Ingredient is added during the heating step in an amount that is from 0.5 to 0.00005 weight percent, preferably from 0.05 to 0.0005 weight percent, and "USP" most preferably from 0.025 to 0.001 weight percent of the total ointment weight. (Source:—United States Pharmacopoeia 24, United States Pharmacopeial Convention, 1999)

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, (ix) fluorides and (x) Parathyroid hormone (PTH) (see, Harrison's Principles of Internal Medicine, $13^{th}$ edition, 1994, published by McGraw Hill Publ., ISBN 0-07-032370-4, pgs. 2172-77; the disclosure of which is incorporated herein by reference). Any one or a combination of these conventional therapies may be used in combination with the method of treatment using compounds of Formula I as taught herein. For example, in a method of treating osteoporosis, the vitamin D receptor modulator compounds of the invention may be administered separately or simultaneously with a conventional therapy. Alternatively, the vitamin D receptor modulator compounds of the invention may be combined with conventional therapeutic agents in a formulation for treatment of osteoporosis such as set out below:

A formulation for treating osteoporosis comprising:

Ingredient (A1): a vitamin D receptor modulator represented by Formula (I), or a pharmaceutically acceptable salt or prodrug derivative thereof;

Ingredient (B1): one or more co-agents that are conventional for treatment osteoporosis selected from the group consisting of: estrogens, androgens, calcium supplements, vitamin D metabolites, thiazide diuretics, calcitonin, bisphosphonates, SERMS, fluorides, and PTH Ingredient (C1): optionally, a carrier or diluent.

Typically useful formulations are those wherein the weight ratio of (A1) to (B1) is from 10:1 to 1:1000 and preferably from 1:1 to 1:100.

Combination Therapy for Psoriasis:

Conventional therapy for psoriasis includes topical glucocorticoids, salicylic acid, crude coal tar, ultraviolet light, and methotrexate (see, Harrison's Principles of Internal Medicine, $13^{th}$ edition, 1994, published by McGraw Hill Publ., ISBN 0-07-032370-4, pgs. 2172-77). Any one or combination of these conventional therapies may be used in combination with the method of treatment using compounds of Formula I as taught herein. For example, in a method of treating psoriasis, the vitamin D receptor modulator compounds of the invention (e.g., as defined by Formula I) may be topically administered separately or simultaneously with a conventional therapy. Alternatively, the vitamin D receptor modulator compounds of the invention may be combined with conventional therapeutic agents in a topically applied formulation for treatment of psoriasis such as set out below:

A formulation for treating psoriasis comprising:

Ingredient (A2): a vitamin D receptor modulator represented by Formula (I), or a pharmaceutically acceptable salt or prodrug derivative thereof;

Ingredient (B2): one or more co-agents that are conventional for treatment psoriasis selected from the group consisting of: topical glucocorticoids, salicylic acid, or crude coal tar.

Ingredient (C2): optionally, a carrier or diluent.

Typically useful formulations are those wherein the weight ratio of (A2) to (B2) is from 1:10 to 1:100000 and preferably from 1:100 to 1:10000.

Experimental Results:

TABLE 2

| Summary of Experimental Results | | | | |
|---|---|---|---|---|
| Test Cmpd.[1] | RXR-VDR heterodimer[2] $EC_{50}$ (nM) | VDR $EC_{50}$ (nM) (Caco-2 cells)[3] | OCN Promoter[4] $EC_{50}$ (nM) | Mouse Hypercal[5] µg/Kg/d |
| Ex. 1 | 40 | 194 | 2.6 | 1000 |
| Ex. 2A | 30.2 | 466 | 6.0 | 300 |
| Ex. 2B | 25.3 | | 18.4 | 1000 |
| Ex. 3 | 0.4 | 35 | 0.1 | <300 |
| Ex. 4 | 105 | 550 | 41 | 1000 |
| Ex. 5 | 1 | 162 | 0.2 | <30 |
| Ex. 6 | 715 | 714 | 104 | |
| Ex. 7 | 2.6 | | 0.7 | 100 |
| Ex. 8 | 2.0 | | 0.6 | 300 |

TABLE 3

| Summary of Experimental Results | | |
|---|---|---|
| Test Cmpd.[1] | Keranocyte Proliferation $IC_{50}$ (nM) | IL-10. $IC_{50}$ (nM) |
| Ex. 1 | 653 | 76 |
| Ex. 2 | 47 | 49 |
| Ex. 3 | 2 | |
| Ex. 4 | >1000 | |
| Ex. 5 | 24 | 5 |

Explanation of Tables 2 and 3 column numerical superscripts:

1. Test Compound numbers refer to the products of the corresponding Example Nos. that is, compounds within the scope of the invention.

2. The RXR-VDR heterodimerization (SaOS-2 cells) test is described in the "Assay" section of the Description, infra.

3. The VDR CTF (Caco-2 cells) test is described in the "Assay" section of the Description, infra.

4. The OCN Promoter test is described in the "Assay" section of the Description, infra.

5. The Mouse Hypercalcemia test is described in the "Assay" section of the Description, infra.

6. The keratinocyte proliferation assay is described in the "Assay" section of the Description, infra.

7. The IL-10 induction assay is described in the "Assay" section of the Description, infra.

Assay Methods

Use of the Assay Methods:

The evaluation of the novel compounds of the invention for osteoporosis and other related diseases is done using a plurality of test results. The use of multiple assays is beneficial since it is preferred that the combined properties of (i) high activity for the vitamin D receptor, and (ii) prevention of hypercalcemia be achieved to effect treating diseases, which are also aspects of this invention. Some of the tests described below are believed related to other tests and measure related properties of compounds. Consequently, a compound may be considered to have utility in the practice of the invention if it meets at least one preferably two or more, if not all, of the acceptance criteria for the above described tests.

The evaluation of the novel compounds of the invention for psoriasis is done using the Keratinocyte Proliferation Assay in combination with other assays that measure inhibition of IL-2 production and stimulation of IL-10 production in peripheral blood mononuclear cells (PBMCs).

Brief Description, Utility and Acceptance Criteria for the Assay Methods:

1. The RXR-VDR Heterodimer Assay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

(1) Materials and Method for RXR-VDR Heterodimerization Assay Transfection

Method: Reagents: FuGENE 6 Transfection Reagent (Roche Cat #1 814 443); Growth Media: D-MEM High Glucose (Gibco BRL Cat #11054-020), 10% heat inactivated FBS, (Gibco BRL Cat#10092-147) 1% antibiotic-antimycotic (Ab-Am); (Gibco BRL Cat #15240-062).

Cells: Grow SaOS-2 cells in T-150 $cm^2$ culture flasks in growth media keeping the density at 5-6×$10^5$ cells/ml. Passage cells 1:3 twice a week. Add Trypsin EDTA (Gibco BRL Cat #25300-020) and incubate. Resuspend cells in plating media and transfer into growth media.

Wash Media: HBSS Low Glucose Without Phenol Red (Gibco BRL Cat #14175-095), 1% Ab-Am. Plating Media: D-MEM Low Glucose Without Phenol Red (Gibco BRL Cat #11054-020), 1% Ab-Am; D-MEM; 10% Stripped FBS (Hyclone Cat#SH30068.03 Lot #AHM9371);

Transfection/Treatment Media: D-MEM Low Glucose Without Phenol Red only; T-150 $cm^2$ culture flask: Use Corning Coastar T-150 $cm^2$ culture flask (Cat #430825) to grow the cells.

Luciferase Assay Reagent: Use Steady-Glo Luciferase Reagent from Promega (Cat #E2550) Consists of: E2533 Assay Substrate, lyophilized product and E2543 Assay Buffer. Thaw at room temperature and store.

Cell Harvesting/Count: Aspirate media from culture flask, rinse cells with HBSS and aspirate. Add trypsin and incubate. When cells appear detached, resuspend cells in growth media. Transfer into a new flask with fresh growth media for passaging the cells. Plate 96 well plates and two extra plates. Mix the cell suspension using pipette. To count the cells using a Hematocytometer.

Plate seeding: Use plating media 10% Stripped FBS in D-MEM Low Glucose, without Phenol Red, 1% Ab-Am. Plate 14 plates @ 165 μl/well. In sterile flask add cell suspension to plating media and mix. Add cells/well. Place the cells in the incubator. Cells should be about 75% confluent prior to transfection. DAY 2: Transfection: Step 1, DNA and Media: Add plain DMEM media to tubes for mixing the DNA; add the Reporter gene pFR-LUC; and add the Gal-4-RXR-DEF and VP16-VDR-LBD. Step 2, FuGENE and Media: Prepare plain DMEM media in a tubes for mixing FuGENE, add FuGENE 6 Transfection Reagent, and incubate. Step 3, FuGENE, DNA and Media Complex: Add FuGENE Media complex from step 2 to DNA Media complex from step 1 and incubate. Step 4, FuGENE, DNA and Media Complex to 96 well plate: Add FuGENE-DNA-Media complex from step 3 to each plate. Incubate.

Day 3: Dosing: Treatment preparation. Allow for transfection time.

Make a stock solution of the compounds in DMSO and vortex until all the compounds have been dissolved. Further dilute in D-MEM (Low Glucose—without Phenol Red) Add compounds in quadruplicate to give desired final volume then incubate.

Day 4: Luciferase Assay: Read the plates after drug treatment. Remove part of media from all the wells and leave remainder. Add Steady-Glo Luciferase Reagent mixture/wells and incubate. Count each well using a Luminescence counter, Top Count NXT by Packard preferably set a delay between plates to reduce the background.

The Caco-2 Cell Co-Transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 nM. Preferred assay results are greater than 1000 nM.

Caco-2 cells, grown in phenol red free, DMEM (Invitrogen, Carlsbad, Calif.) containing 10% charcoal-stripped FBS (Hyclone, Logan, Utah), are transfected with Fugene 6 reagent (Roche Diagnostics, Indianapolis, Ind.). Cells (5000/well) are plated 18 h before transfection in a 96 well plate. The cells are transfected with Gal4-responsive reporter pFRLuc (150 ng, Stratagene, La Jolla Calif.) and the receptor expression vector pGal4-VDR-LBD (10 ng), along with Fugene 6 reagent (0.2 μl/well). The DNA-Fugene complex is formed by incubating the mixture for 30 m at room temperature. The cells are transfected in triplicate for 5 h, and treated with various concentrations of VDR ligands (from 0.01 nM to 10,000 mM concentration range) 18 h post-transfection. The luciferase activity is quantified using Steady-Glo reagent kit (Promega, Madison, Wis.) as per manufacturer's specifications.

The OCN (Osteocalcin) Promoter Assay

The OCN Promoter Assay is an indicator and marker for osteoporosis. Desired assay results are EC50 less than or equal to 325 nM. Preferred assay results are less than 50 nM.

The activation of osteocalcin by VDR ligands is evaluated in a rat osteoblast-like cell line RG-15 (ROS 17/2.8) stably expressing rat osteocalcin promoter fused with luciferase reporter gene. The stable cell lines are established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. *J Biol. Chem.* 275, 999-1006, 2000). Confluent RG-15 cells maintained in DMEM/F-12 medium (3:1) containing 5% FBS, 300 μg/ml G418 and at 37° C. under 5% $CO_2$/95% air atmosphere are trypsinized (0.25% trypsin) and plated into white opaque 96-well cell culture plates (25000 cells/well). After 24 hr, cells (in DMEM/F-12 medium+2% FBS) are treated with various concentrations of compounds, dissolved in DMSO. The final DMSO concentration remains at 0.01% (v/v). After 48 hr treatment, the medium is removed, cells are lysed with 50 μl of lysis buffer (From Luciferase reporter assay system, Roche Diagnostics, Indianapolis, Ind.) and then assayed for luciferase activity using the Luciferase Reporter Gene Assay kit from Boehringer Mannheim as per manufacturer's specifications.

The Mouse Hypercalcemia Assay

The Mouse Hypercalcemia Assay is a six day hypercalcemia test for toxicity and selectivity. Acceptable test results are levels greater than 30 μg/kg/day. Preferred assay results are levels greater than 300 μg/kg/day.

Weanling, virus—antibody-free, five to six weeks old female DBF mice (Harlan, Indianapolis, Ind.) are used for all the studies. Animals are allowed to acclimate to local vivarium conditions for 2 days. Mice are maintained on a 12 hr light/dark cycle at 22° C. with ad lib access to food (TD 5001 with 1.2% Ca and 0.9% P, Teklad, Madison, Wis.) and water. The animals then are divided into groups with 4-5 mice per group. Different doses of test compounds prepared in 10% ethanol and 90% sesame oil, or in an aqueous suspension of sodium lauryl sulfate and CMC (the latter formulation for acidic compounds) are administered to mice orally via gavage for 6 days. $1\alpha$-$25(OH)_2D_3$ 0.5 μg/kg/d was also given to one group of mice as the positive control. Serum ionized calcium is evaluated at 6 hours after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was $P<0.05$. The highest dose that did not cause hypercalcemia, as defined by the 97.5% reference distribution of the control population, is considered "the no effect level".

The Keratinocyte Proliferation Assay

This Assay is indicative for the treatment of psoriasis. An acceptable test result is IC50 value of less than or equal to 300 nM. Preferred assay results are IC50 values of less than 100 nM.

KERtr cells (Human skin keratinocyte are transformed with a retrovirus vector, obtained from ATCC, then are plated in 96-well flat-bottomed plates (3000 cells/well) in 100 μl keratinocyte serum free medium supplemented with bovine pituitary extract in the absence of EGF (Life Technologies, Rockville, Md.) and are incubated at 37° C. for two days. The cells are treated with various concentrations of VDR ligands (ten-fold serial dilution from 10,000 nM to 0.1 nM in triplicate), dissolved in 100 μl keratinocyte serum free medium supplemented with bovine pituitary extract in the absence of EGF and are incubated at 37° C. for 72 hr. BrdU (5-bromo-2'-deoxyuridine) incorporation is analyzed as a measure of DNA replication (Cell proliferation ELISA kit, Roche Diagnostics, Indianapolis, Ind.) and absorbance is measured at 405 μm. Potency values ($IC_{50}$) values were determined as the concentration (nM) of compound that elicited a half-maximal response.

The IL-10 Induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

Isolation of Peripheral Blood Mononuclear Cells (PBMCs):

Collect 50 ml of human blood and dilute with media, RPMI-1640. Add diluted blood to sterile tubes with ficol. Centrifuge the tubes. Discard the top layer and collect the cells from middle layer. Divide all cells into four tubes and add media. Centrifuge. Aspirate off media and resuspend the cells. Collect all cells. Centrifuge at 1200 rpm for 10 m. Resuspend the cells in RPMI-1640 with 2% FBS and then count cells.

Stimulation of PBMC: Prepare TPA in DMSO. Dissolve PHA in water. Plate TPA/PHA treated PBMCs in well plates. Incubate the cells.

Treatment: Prepare all compound dilutions in plain RPMI-1640 media. Add diluted compound and incubate. Sample Collection and assay: Remove all the cells by centrifugation and assay the supernatant for IL-10 by immunoassay using anti-human IL-10 antibody coated beads, as described by the manufacturer (Linco Research Inc., St. Charles, Mo.).

Other Compound Assay Standards

An alternative measure of the therapeutic index (bone efficacy vs Hypercalcemia) of compounds of the invention for treatment of osteoporosis is a numerical ratio calculated as follows:

Dose Threshold needed to induce hypercalcemia divided by Dose Threshold needed for bone efficacy An alternative measure of the therapeutic index (in vivo keratinocyte proliferation vs. hypercalcemia) of compounds of the invention for treatment of psoriasis is a numerical ratio calculated as follows:

Dose Threshold needed to induce hypercalcemia divided by Dose Threshold needed to induce keratinocyte proliferation For the above ratios, Dose Thresholds are determined from dose response curve data.

The CaT1 (Calcium Transporter 1) Assay

The CaT1 Assay is an indicator for the undesirable condition of hypercalcemia. The higher the EC50 values for a compound the less calcemic it will be in vivo. Desired assay results are EC50 greater than or equal to 500 nM. Preferred assay results are greater than 1000 nM.

Human colon carcinoma, Caco-2 cells, maintained in DMEM (high glucose with 25 mM Hepes buffer; Invitrogen, Carlsbad, Calif.) supplemented with 10% FBS (Invitrogen, Carlsbad, Calif.), are plated at 5500 cell per well in a 96-well plate in a total volume of 100 μl/well. The cells are kept in the 96-well plate for 6 days to differentiate them to small intestinal cells that express the calcium transporter, CaT1. On day 3 after plating, old media is removed and replaced with fresh media (150 μl/well). On day 6 the old media is removed and the cells are kept in treatment media (180 μl/well) that contained 10% charcoal stripped FBS (Hyclone, Logan, Utah) in DMEM (low glucose, without phenol red; Invitrogen, Carlsbad, Calif.). The cells are treated with various concentrations of VDR ligands (from 0.01 nM to 10,000 nM concentration range) prepared in treatment media (20 μl/well). Twenty hours post-treatment, total RNA is prepared by RNeasy 96 method as described by the manufacturer (Qiagen, Valencia, Calif.). The RNA is reverse transcribed and amplified for human CaT1 and GAPDH (control) messages by quantitative RT-PCR using ABI PRISM 7900HT Sequence Detection System according to manufacturer's instructions (Applied Biosystems, Foster City, Calif.). Optimized primer pairs and probes for human CaT1 and GAPDH genes are obtained commercially (Applied Biosystems, Foster City, Calif.). Each 20 μl quantitative RT-PCR reaction in a 384-well Taqman PCR plate consists of forward and reverse primers (900 nM), Taqman probe (200 nM), total RNA (4 μl form each well of the 96-well culture plate) and 10 μl of Taqman Universal PCR Master Mix (Roche Diagnostics, Indianapolis, Ind.). Reactions are incubated at 48° C. for 30 m, followed by 10 m at 95° C. and subjected to 40 cycles of PCR (95° C. for 15 seconds followed by 60° C. for 1 m). GAPDH is used as an internal control and its primer and probe set are obtained commercially (Applied Biosystems, Foster City, Calif.).

The invention claimed is:

1. A compound or a pharmaceutically acceptable salt thereof represented by Formula (I):

(I)

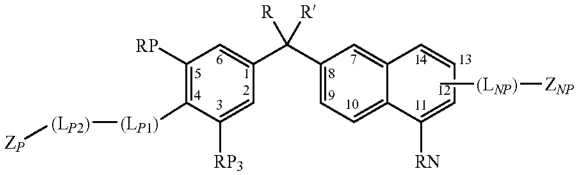

wherein

R and R' are independently $C_1$-$C_5$ alkyl;

$RP_3$ is hydrogen or, $C_1$-$C_5$ alkyl;

RN is hydrogen;

RP is hydrogen;

$(L_{P1})$ is, $(CH_2)_m$—O—;

$(L_{P2})$ is $(CH_2)_m$—CH(OH)—or —$(CH_2)_m$—C(O)—;

$(L_{NP})$ is a bond or —$(CH_2)_m$—C(O)—;

where m is 0-5;

R40 and R41 each is independently selected from hydrogen or $C_1$-$C_5$ alkyl;

$Z_P$ is a branched $C_3$-$C_5$ alkyl;

$Z_{NP}$ is selected from $C_0$-$C_5$ alkyl-$CO_2H$, $C_0$-$C_5$ alkyl-N(R40)(R41), N(R42)-($C_1$-$C_5$ alkyl)$CO_2H$, —N(R42)-($C_1$-$C_5$ alkyl)C(O)($C_1$-$C_5$ alkyl), R42 is a $C_1$-$C_3$ alkyl, and provided that -$(L_{NP})$-$Z_{NP}$ is substituted at either the 12 or 13 position of the naphthalene ring.

2. A compound represented by Formula (C1) to (C8) or a pharmaceutically acceptable salt thereof:

C1)

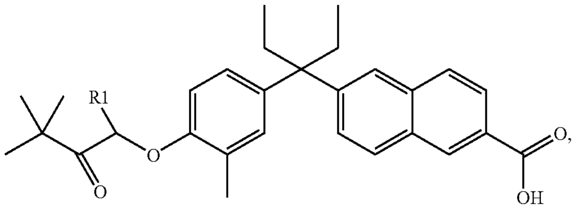

-continued

C2)

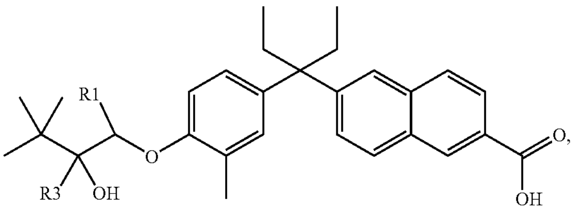

C3)

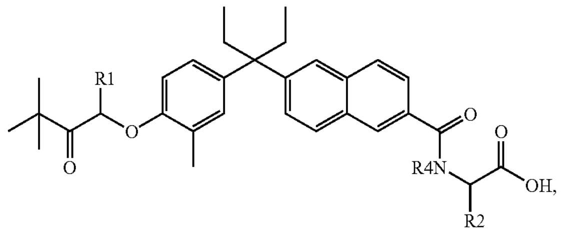

C4)

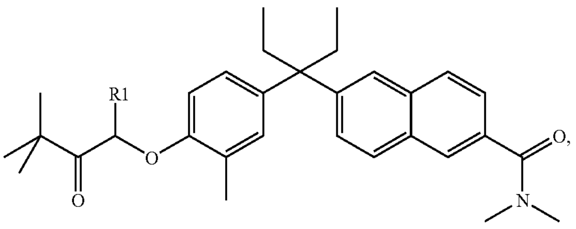

C5)

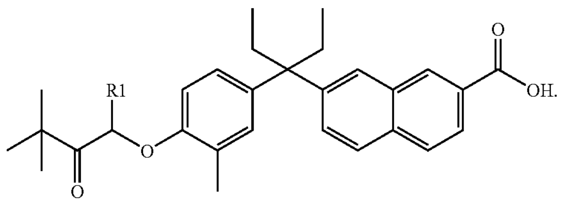

C6)

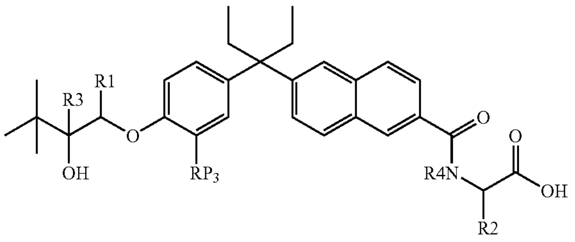

C7)

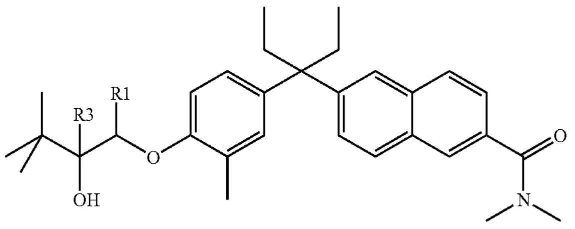

-continued

C8)

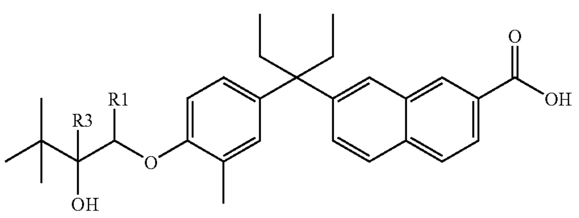

wherein R1 is H, methyl, or ethyl; R2 is H or methyl; R3 is H, methyl, or ethyl, and R4 is H or methyl.

3. The compound of claim 2 represented by formulae (C1) to (C8) or a pharmaceutically acceptable salt thereof: where R1 is a methyl, or ethyl; and R2 is H or methyl.

4. The compound of claim 2 represented by the structural Formula (C2) or a pharmaceutically acceptable salt thereof.

5. A compound of claim 2 represented by the structural Formula (C1) or a pharmaceutically acceptable salt thereof.

6. A salt of the compound of claim 1 wherein the counter ion is sodium or potassium.

7. A pharmaceutical formulation comprising the compound of claim 1, or a pharmaceutically acceptable salt thereof, either with a pharmaceutically acceptable carrier or diluent.

8. A formulation according to claim 7 for treating osteoporosis comprising:

a compound of Formula I, or a pharmaceutical acceptable salt, and one or more co-agents selected from the group consisting of: estrogens, androgens, calcium supplements, vitamin D metabolites, thiazide diuretics, calcitonin, bisphosphonates, SERMS, fluorides.

9. A pharmaceutical composition comprising a compound of Formula I of claim 1, or a pharmaceutically acceptable salt thereof, for treating osteoporous.

10. A method of treating a mammal to treat or alleviate the pathological effects of Osteoporosis or Psoriasis; wherein the method comprises administering a pharmaceutically effective amount of at least one compound according to claim 1, or a pharmaceutically acceptable salt thereof.

11. The method of claim 10 for the treatment of psoriasis.

12. The method of claim 10 for the treatment of osteoporosis.

* * * * *